US010415071B2

(12) United States Patent
Ochiai et al.

(10) Patent No.: US 10,415,071 B2
(45) Date of Patent: Sep. 17, 2019

(54) METHOD FOR PRODUCING STEVIOL AND STEVIOL GLYCOSIDE USING AOBGL3 HOMOLOG

(71) Applicant: SUNTORY HOLDINGS LIMITED, Osaka (JP)

(72) Inventors: Misa Ochiai, Kyoto (JP); Eiichiro Ono, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days.

(21) Appl. No.: 15/770,896

(22) PCT Filed: Oct. 28, 2016

(86) PCT No.: PCT/JP2016/082028
§ 371 (c)(1),
(2) Date: Apr. 25, 2018

(87) PCT Pub. No.: WO2017/073716
PCT Pub. Date: May 4, 2017

(65) Prior Publication Data
US 2018/0312892 A1 Nov. 1, 2018

(30) Foreign Application Priority Data

Oct. 30, 2015 (JP) ................. 2015-214256

(51) Int. Cl.
C12P 19/14 (2006.01)
C12N 9/42 (2006.01)
C12P 7/02 (2006.01)
C12P 15/00 (2006.01)
C12N 9/24 (2006.01)
C12N 15/09 (2006.01)
C07C 61/29 (2006.01)
C07H 3/02 (2006.01)
C12N 15/80 (2006.01)

(52) U.S. Cl.
CPC ............ C12P 19/14 (2013.01); C12N 9/2445 (2013.01); C12P 7/02 (2013.01); C12P 15/00 (2013.01); C07C 61/29 (2013.01); C07H 3/02 (2013.01); C12N 9/24 (2013.01); C12N 15/09 (2013.01); C12N 15/80 (2013.01); C12Y 302/01021 (2013.01)

(58) Field of Classification Search
None
See application file for complete search history.

(56) References Cited

U.S. PATENT DOCUMENTS

2004/0248258 A1 12/2004 Maiyuran et al.
2013/0071887 A1* 3/2013 Wehrli ................ C12P 7/42
435/127
2015/0218533 A1 8/2015 Ono

FOREIGN PATENT DOCUMENTS

CN 102827891 A 12/2012
JP 10-276775 A 10/1998
JP 2013-516963 A 5/2013
WO 2013/180306 A1 12/2013

OTHER PUBLICATIONS

Accession Q2U8V9. Jan. 24, 2006. (Year: 2006).*
Accession Q2U8V9—Alignment to SEQ ID No. 4. Jan. 24, 2006. (Year: 2006).*
Chica et al. Curr Opin Biotechnol. Aug. 2005;16(4):378-84. (Year: 2005).*
Singh et al. Curr Protein Pept Sci. 2017, 18, 1-11 (Year: 2017).*
"Beta-glucosidase [Aspergillus oryzae RIB40]", Accession No. XP_001823139; https://www.ncbi.nlm.nih.gov/protein/XP_001823139, Mar. 3, 2011.
Ko et al., "Mass Production of Rubusoside Using a Novel Stevioside-Specific β-Glucosidase from Aspergillus aculeatus", Journal of Agricultural and Food Chemistry, vol. 60, pp. 6210-6216 (2012).
Kasai et al., "Sweet Diterpene-Glycosides of Leaves of Stevia rebaudiana Bertoni—Synthesis and Structure-Sweetness Relationship of Rebaudiosides-A, -D, -E and Their Related Glycosides—", Journal of the Chemical Society of Japan, (5) pp. 726-735 (1981), including English language Abstract.
Miyashiro, "Purification and Properties of Stevioside Hydrolyzing Enzyme from Raw Soy Sauce", Journal of the Japanese Society for Food Science and Technology, vol. 37, No. 5, pp. 369-374 (1990), including English language Abstract.
Sakamoto et al., "Quantitative Analysis of Stevioside", Journal of the Pharmaceutical Society of Japan, 95 (12), pp. 1507-1510 (1975), including English language Abstract.
Bennett et al., "Biosynthesis of Steviol From (--)-Kaurene", Phytochemistry, vol. 6, No. 8, pp. 1107-1110 (1967).
Ma et al., "Biological Conversion of Stevioside to Steviol by Aspergillus aculeatus and the Purification of Rebaudioside A", Acta Microbiologica Sinica, 54 (1), pp. 62-68 (2014), including English language Abstract.
Langston et al., "Substrate Specificity of Aspergillus oryzae Family 3 β-glucosidase", Biochimica et Biophysica Acta, vol. 1764, pp. 972-978 (2006).
International Search Report for PCT/JP2016/082028, with English translation, dated Jan. 24, 2017.

* cited by examiner

Primary Examiner — Christian L Fronda
(74) Attorney, Agent, or Firm — Greenblum & Bernstein, P.L.C.

(57) ABSTRACT

The present invention provides a method for preparing a steviol glycoside and/or steviol comprising reacting glycosidase AOBGL1 and/or AOBGL3 or a variant thereof with a steviol glycoside having at least one monoglucoside bond and/or monoglucosyl ester bond, thereby cleaving said monoglucoside bond and/or monoglucosyl ester bond.

13 Claims, 2 Drawing Sheets

Specification includes a Sequence Listing.

[Figure 1]
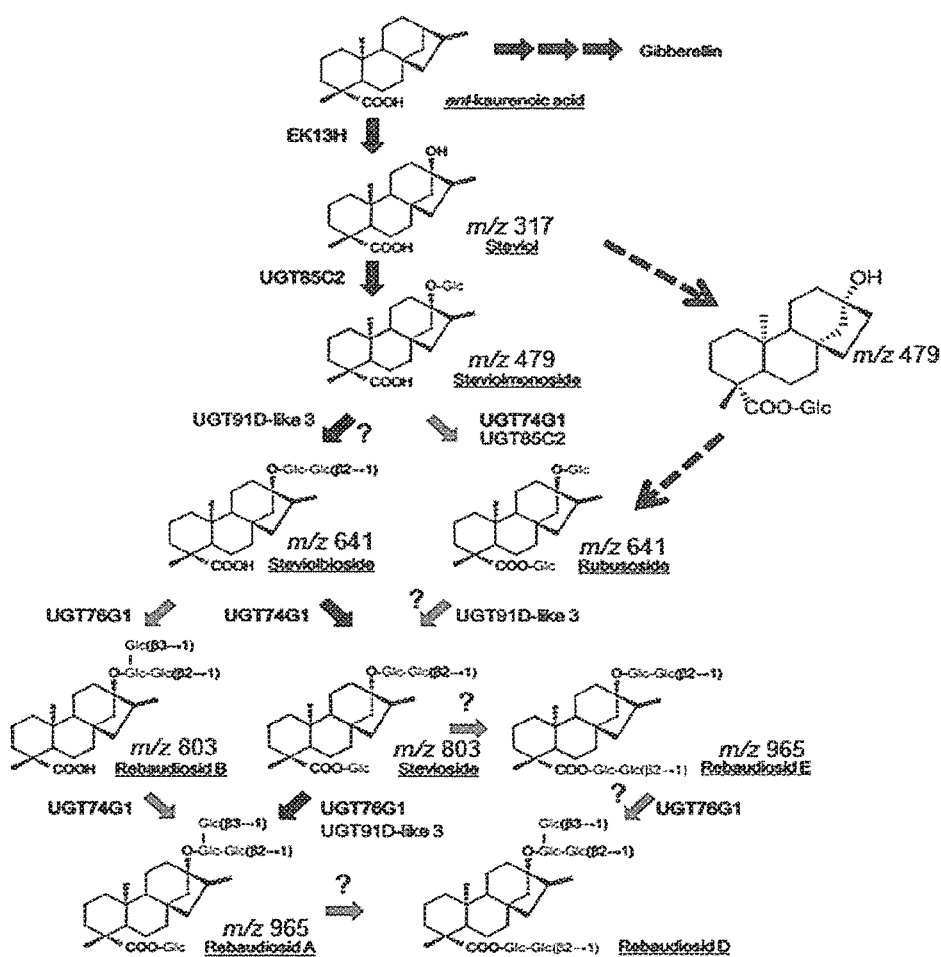

MF(ALPHA)1 signal peptide

5' ATGAGATTTC CTTCAATTTT TACTGCAGTT TTATTCGCAG CATCCTCCGC ATTAGCT 3'
  M  R  F  P  S  I  F  T  A  V  L  F  A  A  S  S  A  L  A

B

PHO5 signal peptide

5' ATGTTTAAAT CTGTTGTTTA TTCAATTTTA GCCGCTTCTT TGGCCAATGC A 3'
  M  F  K  S  V  V  Y  S  I  L  A  A  S  L  A  N  A

C

SUC2 signal peptide

5' ATGCTTTTGC AAGCTTTCCT TTTCCTTTTG GCTGGTTTTG CAGCCAAAAT ATCTGCA 3'
  M  L  L  Q  A  F  L  F  L  L  A  G  F  A  A  K  I  S  A

SEQUENCE LISTING

<160> NUMBER OF SEQ ID NOS: 36

<210> SEQ ID NO 1
<211> LENGTH: 2340
<212> TYPE: DNA
<213> ORGANISM: Aspergillus oryzae var. Brunneus

<400> SEQUENCE: 1
atggtttccg gtgtctttac gaaggggggtt ctgctcctgg gcctcttgtc gggtctggct      60

```
cttggtcaag atgagaagcc tcgctacaag gaccccagtg ttccagtgga ggagcgcgtc      120
actgatctgc tgggtcgtat gacgctcgag gagaagatgt ctcaattgat tcagggcgac      180
atcaccaatt ggatgaatga gactactgga gaattcaacc tcacgggttt ggaatggagt      240
acgaaaatga ggggtggaat gttctacgtc ggatatccgg tgccttggga ttacatcgca      300
gacaatgtca agaaagctca ggactatatt ctccaaaaca cgactctcgg gattcccgcc      360
attgttcaga cagaatctct tcacggattc ctcatcggta atgcaacgat ctataactct      420
cccatcgggt tcgcatgctc gttcaacccg gagcttatcg agaaaatggc acgcctcatc      480
ggtcaggagg cctcagccct tggggttaac cacgtaatgg accagtggt tgatctcgcc      540 cgtgaattgc gatttggaag agtcgaagag acgtacggtg aagacccgtt ccttgcagga      600
gaaattggat accactatac caagggcatc aaaagccaca atatctccgc caacgtcaag      660
cactttgtgg gattctccca acccgaacaa ggtctcaaca ctgcacctgt ccacggagga      720
gagagatatc tgcgcacgac ttggttgcca tcattcaagc gcgccattat ggatgccgga      780
gcgtggagta tcatgagtgc gtaccactca tacgacggta tccccgccgt agccgactac      840
cacaccctca ccgaaatcct ccgcgaagaa tggggctaca aatactgggt aaccagtgac      900
gccggcgcca gcgacagagt ctgcacagcc ttcaaactct gccgcgcgga ccccatcgac      960
aaggaagccg ttacacttgc catcctccca gccggaaacg acgtcgaaat gggcggtggc     1020
tcatacaact cgaaacgat catcgacctg gtcaatgccg gcaagctcga tattgaaatc     1080
gtcaacacgg cggtatcccg tgtgctccgt gcgaagttcg aaatgggcct cttcgagaac     1140
ccctacaatg ctgctccggc gtctgagtgg aacaagctca tccatactca ggaggctgtt     1200
gatcttgccc gtgagctgga tcgggagtcg attgttctgc tggagaatca tgataatgcg     1260
cttccgttga agaagagtgg tagcatcgct gttatcgggc ctatgccgca tgggtttatg     1320
aattatggag actacgtcgt ctacgaaagc cagtaccgcg gcgtgacccc cttggacggc     1380
atcaaagccg ccgtcggcga caaggcaacg atcaactacg cccagggctg cgaacgctgg     1440
agcaacgacc aatccggctt cgccgaggca gtcgaagcag ccaagaagtc cgacgtagca     1500
gtcgtagtcg tgggtacctg gtctcgcgac cagaaggagc tctgggccgg tctcaacgca     1560
acaaccggcg aacacgtcga cgtaaacagc ctcagcctcg tcggcgccca gcccccctc      1620 atcaaagcaa tcatcgacac aggcgttccc accgtggtcg tcctctccag cggcaagccc     1680
atcacagaac cctggctctc gaacaacacc gccgcactcg tccagcaatt ctaccctcc      1740 gagcaaggcg aaatgccct cgccgacgtc ctcttcggcg actataaccc ctccggaaaa     1800
ctctccgtca gcttcccgca ctccgttggc gatctgccca tctactacga ttatctgaac     1860
tcggcgcgcg agatcggtga tgctgggtat atttattcga atggcacgct ggagttcggt     1920
caccagtatg cgcttggcaa tcccaaggcg tggtatccct cgggtatgg gaagagttat     1980 tcgagcttcg agtatggggc tgtgaagctt gataagacga atgtgacgga ggcggatacg     2040
gttactgtta gtgttgatgt gaagaatacg gatgccacga gggagggcac ggaggttgtg     2100
caggtgtatg ttgttgatga ggttgcgtcg gttgtggtgc cgaatcggtt gctcaagggg     2160
ttcaagaagg ttgttattcc tgctgggcag accaagacgg tggagattcc gttgaaggtg     2220
caggatttgg ggctgtggaa tgtgcgcatg aagtatgttg ttgagcctgg ggcttttggt     2280
gtgctggtgg gaagtagctc ggaggatatt cggggcaatg ctactttcta tgtgcagtga     2340
```

```
<210> SEQ ID NO 2
<211> LENGTH: 2959
```

<212> TYPE: DNA
<213> ORGANISM: Aspergillus oryzae var. Brunneus

<400> SEQUENCE: 2

| | | | | | |
|---|---|---|---|---|---|
| atggtttccg | gtgtctttac | gaaggggtt | ctgctcctgg | gcctcttgtc | gggtctggct | 60 |
| cttggtcaag | atgagaagcc | tcgctacaag | gaccccagtg | ttccagtgga | ggagcgcgtc | 120 |
| actgatctgc | tgggtcgtat | gacgctcgag | gagaagatgt | ctcaattgat | tcagggtgcg | 180 |
| attgaattg | tctcgttttt | accaacagga | ggtactgatt | gatcatcgca | ggcgacatca | 240 |
| ccaattggat | gaatgagact | actggagaat | tcaacctcac | gggtttggaa | tggagtacga | 300 |
| aaatgagggg | tggaatgttc | tacggtaggc | aactaacctt | acaggattgt | tatcacagta | 360 |
| gctaactagc | tatggctttc | agtcggatat | ccggtgcctt | gggattacat | cgcagacaat | 420 |
| gtcaagaaag | ctcaggacta | tattctccaa | aacacgactc | tcgggattcc | cgccattgtt | 480 |
| cagacagaat | gtatgttcta | gtcatgttcg | attcgctgaa | ctctgcgctg | ataatctttg | 540 |
| ctttgatagc | tcttcacgga | ttcctcatcg | gtaatgcaac | gatctataac | tctcccatcg | 600 |
| ggttcgcatg | ctcgttcaac | ccggaggtga | gcccatcctt | cctgagacct | gtcagacaag | 660 |
| gcccaccaga | acacaaagct | aataaacaca | actccagctt | atcgagaaaa | tggcacgcct | 720 |
| catcggtcag | gaggcctcag | cccttggggt | taaccacgta | atgggaccag | tggttgatct | 780 |
| cgcccgtgaa | ttgcgatttg | gaagagtaag | ccttatactt | catttcctca | atagaacaga | 840 |
| cctaaaagtc | atgtacaggt | cgaagagacg | tacggtgaag | acccgttcct | gcaggagaa | 900 |
| attggatacc | actataccaa | gggcatccaa | agccacaata | tctccgccaa | cgtcaagcac | 960 |
| tttgtgggat | tctcccaacc | cgaacaaggt | ctcaacactg | cacctgtcca | cggaggagag | 1020 |
| agatatctgc | gcacgacgta | tgtactttgt | tctagtcaac | tagagttcta | cccagcaatg | 1080 |
| actaaccaag | tcgatacagt | tggttgccat | cattcaagcg | cgccattatg | gatgccggag | 1140 |
| cgtggagtat | catgagtgcg | taccactcgt | aagtatacat | tgtgccttac | atattgtctt | 1200 |
| tatttaatca | gtattaacca | aaaacagata | cgacggtatc | cccgccgtag | ccgactacca | 1260 |
| caccctcacc | gaaatcctcc | gcgaagaatg | gggctacaaa | tactgggtaa | ccagtgacgc | 1320 |
| cggcgccagc | gacagagtct | gcacagcctt | caaactctgc | cgcgcggacc | ccatcgacaa | 1380 |
| ggaagccgtt | acacttgcca | tcctcccagc | cggaaacgac | gtcgaaatgg | cggtggctc | 1440 |
| atagtaagtg | tcaccctccc | agtcagttga | taatcgtcta | acacaagatt | agcaacttcg | 1500 |
| aaacgatcat | cgacctggtc | aatgccggca | agctcgatat | tgaaatcgtc | aacacggcgg | 1560 |
| tatcccgtgt | gctccgtgcg | aagttcgaaa | tgggcctctt | cgagaacccc | tacaatgctg | 1620 |
| ctccggcgtc | tgagtggaac | aagctcatcc | atactcagga | ggctgttgat | cttgcccgtg | 1680 |
| agctggatcg | ggagtcgatt | gttctgctgg | agaatcatga | taatgcgctt | ccgttgaaga | 1740 |
| agagtggtag | catcgctgtt | atcgggccta | tggcgcatgg | gtttatgaat | gtgagttttt | 1800 |
| ctagtcttct | tgcggttcat | cggagatgaa | tagcacatgc | atgagacagc | agggggcaatg | 1860 |
| ctaactaaca | cacacacagt | atggagacta | cgtcgtctac | gaaagccagt | accgcggcgt | 1920 |
| gacccccttg | gacggcatca | agccgccgt | cggcgacaag | gcaacgatca | actacgccca | 1980 |
| gggctgcgaa | cgctggagca | cgaccaatc | cggcttcgcc | gaggcagtcg | aagcagccaa | 2040 |
| gaagtccgac | gtagcagtcg | tagtcgtggg | tacctggtct | cgcgaccaga | aggagctctg | 2100 |
| ggccggtctc | aacgcaacgt | aaaccacccc | cttccctcca | ccccaaaaca | acttggatag | 2160 |
| aaaactaaca | aaggaccta | gaaccggcga | acacgtcgac | gtaaacagcc | tcagcctcgt | 2220 |

-continued

```
cggcgcccaa gcccccctca tcaaagcaat catcgacaca ggcgttccca ccgtggtcgt    2280
cctctccagc ggcaagccca tcacagaacc ctggctctcg aacaacaccg ccgcactcgt    2340
ccagcaattc taccoctccg agcaaggcgg aaatgccctc gccgacgtcc tcttcggcga    2400
ctataacccc tccggaaaac tctccgtcag cttcccgcac tccgttggcg atctgcccat    2460
ctactacgat tatctgaact cggcgcgcga gatcggtgat gctgggtata tttattcgaa    2520
tggcacgctg gagttcggtc accagtatgc gcttggcaat cccaaggcgt ggtatccctt    2580
cgggtatggg aagagttatt cgagcttcga gtatggggct gtgaagcttg ataagacgaa    2640
tgtgacggag gcggatacgg ttactgttag tgttgatgtg aagaatacgg atgccacgag    2700
ggagggcacg gaggttgtgc aggtgtatgt tgttgatgag gttgcgtcgg ttgtggtgcc    2760
gaatcggttg ctcaaggggt tcaagaaggt tgttattcct gctgggcaga ccaagacggt    2820
ggagattccg ttgaaggtgc aggatttggg gctgtggaat gtgcgcatga agtatgttgt    2880
tgagcctggg gcttttggtg tgctggtggg aagtagctcg gaggatattc ggggcaatgc    2940
tactttctat gtgcagtga                                                 2959
```

```
<210> SEQ ID NO 3
<211> LENGTH: 779
<212> TYPE: PRT
<213> ORGANISM: Aspergillus oryzae var. Brunneus

<400> SEQUENCE: 3

Met Val Ser Gly Val Phe Thr Lys Gly Val Leu Leu Gly Leu Leu
1               5                   10                  15

Ser Gly Leu Ala Leu Gly Gln Asp Glu Lys Pro Arg Tyr Lys Asp Pro
                20                  25                  30

Ser Val Pro Val Glu Glu Arg Val Thr Asp Leu Leu Gly Arg Met Thr
            35                  40                  45

Leu Glu Glu Lys Met Ser Gln Leu Ile Gln Gly Asp Ile Thr Asn Trp
        50                  55                  60

Met Asn Glu Thr Thr Gly Glu Phe Asn Leu Thr Gly Leu Glu Trp Ser
65                  70                  75                  80

Thr Lys Met Arg Gly Gly Met Phe Tyr Val Gly Tyr Pro Val Pro Trp
                85                  90                  95

Asp Tyr Ile Ala Asp Asn Val Lys Lys Ala Gln Asp Tyr Ile Leu Gln
            100                 105                 110

Asn Thr Thr Leu Gly Ile Pro Ala Ile Val Gln Thr Glu Ser Leu His
        115                 120                 125

Gly Phe Leu Ile Gly Asn Ala Thr Ile Tyr Asn Ser Pro Ile Gly Phe
    130                 135                 140

Ala Cys Ser Phe Asn Pro Glu Leu Ile Glu Lys Met Ala Arg Leu Ile
145                 150                 155                 160

Gly Gln Glu Ala Ser Ala Leu Gly Val Asn His Val Met Gly Pro Val
                165                 170                 175

Val Asp Leu Ala Arg Glu Leu Arg Phe Gly Arg Val Glu Glu Thr Tyr
            180                 185                 190

Gly Glu Asp Pro Phe Leu Ala Gly Glu Ile Gly Tyr His Tyr Thr Lys
        195                 200                 205

Gly Ile Gln Ser His Asn Ile Ser Ala Asn Val Lys His Phe Val Gly
    210                 215                 220

Phe Ser Gln Pro Glu Gln Gly Leu Asn Thr Ala Pro Val His Gly Gly
225                 230                 235                 240
```

-continued

```
Glu Arg Tyr Leu Arg Thr Thr Trp Leu Pro Ser Phe Lys Arg Ala Ile
                245                 250                 255

Met Asp Ala Gly Ala Trp Ser Ile Met Ser Ala Tyr His Ser Tyr Asp
            260                 265                 270

Gly Ile Pro Ala Val Ala Asp Tyr His Thr Leu Thr Glu Ile Leu Arg
        275                 280                 285

Glu Glu Trp Gly Tyr Lys Tyr Trp Val Thr Ser Asp Ala Gly Ala Ser
    290                 295                 300

Asp Arg Val Cys Thr Ala Phe Lys Leu Cys Arg Ala Asp Pro Ile Asp
305                 310                 315                 320

Lys Glu Ala Val Thr Leu Ala Ile Leu Pro Ala Gly Asn Asp Val Glu
                325                 330                 335

Met Gly Gly Gly Ser Tyr Asn Phe Glu Thr Ile Ile Asp Leu Val Asn
            340                 345                 350

Ala Gly Lys Leu Asp Ile Glu Ile Val Asn Thr Ala Val Ser Arg Val
        355                 360                 365

Leu Arg Ala Lys Phe Glu Met Gly Leu Phe Glu Asn Pro Tyr Asn Ala
    370                 375                 380

Ala Pro Ala Ser Glu Trp Asn Lys Leu Ile His Thr Gln Glu Ala Val
385                 390                 395                 400

Asp Leu Ala Arg Glu Leu Asp Arg Glu Ser Ile Val Leu Leu Glu Asn
                405                 410                 415

His Asp Asn Ala Leu Pro Leu Lys Lys Ser Gly Ser Ile Ala Val Ile
            420                 425                 430

Gly Pro Met Ala His Gly Phe Met Asn Tyr Gly Asp Tyr Val Val Tyr
        435                 440                 445

Glu Ser Gln Tyr Arg Gly Val Thr Pro Leu Asp Gly Ile Lys Ala Ala
    450                 455                 460

Val Gly Asp Lys Ala Thr Ile Asn Tyr Ala Gln Gly Cys Glu Arg Trp
465                 470                 475                 480

Ser Asn Asp Gln Ser Gly Phe Ala Glu Ala Val Glu Ala Ala Lys Lys
                485                 490                 495

Ser Asp Val Ala Val Val Val Gly Thr Trp Ser Arg Asp Gln Lys
            500                 505                 510

Glu Leu Trp Ala Gly Leu Asn Ala Thr Thr Gly Glu His Val Asp Val
    515                 520                 525

Asn Ser Leu Ser Leu Val Gly Ala Gln Ala Pro Leu Ile Lys Ala Ile
530                 535                 540

Ile Asp Thr Gly Val Pro Thr Val Val Leu Ser Ser Gly Lys Pro
                545                 550                 555                 560

Ile Thr Glu Pro Trp Leu Ser Asn Asn Thr Ala Ala Leu Val Gln Gln
            565                 570                 575

Phe Tyr Pro Ser Glu Gln Gly Asn Ala Leu Ala Asp Val Leu Phe
        580                 585                 590

Gly Asp Tyr Asn Pro Ser Gly Lys Leu Ser Val Ser Phe Pro His Ser
    595                 600                 605

Val Gly Asp Leu Pro Ile Tyr Tyr Asp Tyr Leu Asn Ser Ala Arg Glu
610                 615                 620

Ile Gly Asp Ala Gly Tyr Ile Tyr Ser Asn Gly Thr Leu Glu Phe Gly
625                 630                 635                 640

His Gln Tyr Ala Leu Gly Asn Pro Lys Ala Trp Tyr Pro Phe Gly Tyr
                645                 650                 655

Gly Lys Ser Tyr Ser Ser Phe Glu Tyr Gly Ala Val Lys Leu Asp Lys
```

-continued

```
                660               665               670
Thr Asn Val Thr Glu Ala Asp Thr Val Thr Val Ser Val Asp Val Lys
            675               680               685

Asn Thr Asp Ala Thr Arg Glu Gly Thr Glu Val Val Gln Val Tyr Val
            690               695               700

Val Asp Glu Val Ala Ser Val Val Val Pro Asn Arg Leu Leu Lys Gly
705               710               715               720

Phe Lys Lys Val Val Ile Pro Ala Gly Gln Thr Lys Thr Val Glu Ile
                725               730               735

Pro Leu Lys Val Gln Asp Leu Gly Leu Trp Asn Val Arg Met Lys Tyr
            740               745               750

Val Val Glu Pro Gly Ala Phe Gly Val Leu Val Gly Ser Ser Ser Glu
            755               760               765

Asp Ile Arg Gly Asn Ala Thr Phe Tyr Val Gln
            770               775

<210> SEQ ID NO 4
<211> LENGTH: 757
<212> TYPE: PRT
<213> ORGANISM: Aspergillus oryzae var. Brunneus

<400> SEQUENCE: 4

Gln Asp Glu Lys Pro Arg Tyr Lys Asp Pro Ser Val Pro Val Glu Glu
1               5                  10                  15

Arg Val Thr Asp Leu Leu Gly Arg Met Thr Leu Glu Glu Lys Met Ser
                20                  25                  30

Gln Leu Ile Gln Gly Asp Ile Thr Asn Trp Met Asn Glu Thr Thr Gly
            35                  40                  45

Glu Phe Asn Leu Thr Gly Leu Glu Trp Ser Thr Lys Met Arg Gly Gly
50                  55                  60

Met Phe Tyr Val Gly Tyr Pro Val Pro Trp Asp Tyr Ile Ala Asp Asn
65                  70                  75                  80

Val Lys Lys Ala Gln Asp Tyr Ile Leu Gln Asn Thr Thr Leu Gly Ile
                85                  90                  95

Pro Ala Ile Val Gln Thr Glu Ser Leu His Gly Phe Leu Ile Gly Asn
            100                 105                 110

Ala Thr Ile Tyr Asn Ser Pro Ile Gly Phe Ala Cys Ser Phe Asn Pro
            115                 120                 125

Glu Leu Ile Glu Lys Met Ala Arg Leu Ile Gly Gln Glu Ala Ser Ala
130                 135                 140

Leu Gly Val Asn His Val Met Gly Pro Val Val Asp Leu Ala Arg Glu
145                 150                 155                 160

Leu Arg Phe Gly Arg Val Glu Glu Thr Tyr Gly Glu Asp Pro Phe Leu
                165                 170                 175

Ala Gly Glu Ile Gly Tyr His Tyr Thr Lys Gly Ile Gln Ser His Asn
            180                 185                 190

Ile Ser Ala Asn Val Lys His Phe Val Gly Phe Ser Gln Pro Glu Gln
            195                 200                 205

Gly Leu Asn Thr Ala Pro Val His Gly Gly Glu Arg Tyr Leu Arg Thr
210                 215                 220

Thr Trp Leu Pro Ser Phe Lys Arg Ala Ile Met Asp Ala Gly Ala Trp
225                 230                 235                 240

Ser Ile Met Ser Ala Tyr His Ser Tyr Asp Gly Ile Pro Ala Val Ala
                245                 250                 255
```

```
Asp Tyr His Thr Leu Thr Glu Ile Leu Arg Glu Glu Trp Gly Tyr Lys
            260                 265                 270

Tyr Trp Val Thr Ser Asp Ala Gly Ala Ser Asp Arg Val Cys Thr Ala
        275                 280                 285

Phe Lys Leu Cys Arg Ala Asp Pro Ile Asp Lys Glu Ala Val Thr Leu
    290                 295                 300

Ala Ile Leu Pro Ala Gly Asn Asp Val Glu Met Gly Gly Ser Tyr
305                 310                 315                 320

Asn Phe Glu Thr Ile Ile Asp Leu Val Asn Ala Gly Lys Leu Asp Ile
                325                 330                 335

Glu Ile Val Asn Thr Ala Val Ser Arg Val Leu Arg Ala Lys Phe Glu
            340                 345                 350

Met Gly Leu Phe Glu Asn Pro Tyr Asn Ala Ala Pro Ala Ser Glu Trp
        355                 360                 365

Asn Lys Leu Ile His Thr Gln Glu Ala Val Asp Leu Ala Arg Glu Leu
    370                 375                 380

Asp Arg Glu Ser Ile Val Leu Glu Asn His Asp Asn Ala Leu Pro
385                 390                 395                 400

Leu Lys Lys Ser Gly Ser Ile Ala Val Ile Gly Pro Met Ala His Gly
                405                 410                 415

Phe Met Asn Tyr Gly Asp Tyr Val Val Tyr Glu Ser Gln Tyr Arg Gly
            420                 425                 430

Val Thr Pro Leu Asp Gly Ile Lys Ala Ala Val Gly Asp Lys Ala Thr
        435                 440                 445

Ile Asn Tyr Ala Gln Gly Cys Glu Arg Trp Ser Asn Asp Gln Ser Gly
    450                 455                 460

Phe Ala Glu Ala Val Glu Ala Ala Lys Lys Ser Asp Val Ala Val Val
465                 470                 475                 480

Val Val Gly Thr Trp Ser Arg Asp Gln Lys Glu Leu Trp Ala Gly Leu
                485                 490                 495

Asn Ala Thr Thr Gly Glu His Val Asp Val Asn Ser Leu Ser Leu Val
            500                 505                 510

Gly Ala Gln Ala Pro Leu Ile Lys Ala Ile Ile Asp Thr Gly Val Pro
        515                 520                 525

Thr Val Val Val Leu Ser Ser Gly Lys Pro Ile Thr Glu Pro Trp Leu
    530                 535                 540

Ser Asn Asn Thr Ala Ala Leu Val Gln Gln Phe Tyr Pro Ser Glu Gln
545                 550                 555                 560

Gly Gly Asn Ala Leu Ala Asp Val Leu Phe Gly Asp Tyr Asn Pro Ser
                565                 570                 575

Gly Lys Leu Ser Val Ser Phe Pro His Ser Val Gly Asp Leu Pro Ile
            580                 585                 590

Tyr Tyr Asp Tyr Leu Asn Ser Ala Arg Glu Ile Gly Asp Ala Gly Tyr
        595                 600                 605

Ile Tyr Ser Asn Gly Thr Leu Glu Phe Gly His Gln Tyr Ala Leu Gly
    610                 615                 620

Asn Pro Lys Ala Trp Tyr Pro Phe Gly Tyr Gly Lys Ser Tyr Ser Ser
625                 630                 635                 640

Phe Glu Tyr Gly Ala Val Lys Leu Asp Lys Thr Asn Val Thr Glu Ala
                645                 650                 655

Asp Thr Val Thr Val Ser Val Asp Val Lys Asn Thr Asp Ala Thr Arg
            660                 665                 670

Glu Gly Thr Glu Val Val Gln Val Tyr Val Val Asp Glu Val Ala Ser
```

|   |   |   | 675 |   |   |   | 680 |   |   |   | 685 |   |
|---|---|---|---|---|---|---|---|---|---|---|---|---|
| Val | Val | Val | Pro | Asn | Arg | Leu | Leu | Lys | Gly | Phe | Lys | Lys | Val | Val | Ile |
|   |   |   | 690 |   |   |   | 695 |   |   |   | 700 |   |

| Pro | Ala | Gly | Gln | Thr | Lys | Thr | Val | Glu | Ile | Pro | Leu | Lys | Val | Gln | Asp |
| 705 |   |   |   | 710 |   |   |   | 715 |   |   |   | 720 |

| Leu | Gly | Leu | Trp | Asn | Val | Arg | Met | Lys | Tyr | Val | Val | Glu | Pro | Gly | Ala |
|   |   |   |   | 725 |   |   |   | 730 |   |   |   | 735 |

| Phe | Gly | Val | Leu | Val | Gly | Ser | Ser | Ser | Glu | Asp | Ile | Arg | Gly | Asn | Ala |
|   |   |   | 740 |   |   |   | 745 |   |   |   | 750 |

| Thr | Phe | Tyr | Val | Gln |
|   |   |   | 755 |

<210> SEQ ID NO 5
<211> LENGTH: 2586
<212> TYPE: DNA
<213> ORGANISM: Aspergillus oryzae var. Brunneus

<400> SEQUENCE: 5

```
atgaagcttg gttggatcga ggtggccgca ttggcggctg cctcagtagt cagtgccaag      60
gatgatctcg cgtactcccc tcctttctac ccttccccat gggcagatgg tcagggtgaa     120
tgggcggaag tatacaaacg cgctgtagac atagtttccc agatgacgtt gacagagaaa     180
gtcaacttaa cgactggaac aggatggcaa ctagagaggt gtgttggaca aactggcagt     240
gttcccagac tcaacatccc cagcttgtgt ttgcaggata gtcctcttgg tattcgtttc     300
tcggactaca attcagcttt ccctgcgggt gttaatgtcg ctgccacctg ggacaagacg     360
ctcgcctacc ttcgtggtca ggcaatgggt gaggagttca gtgataaggg tattgacgtt     420
cagctgggtc ctgctgctgg ccctctcggt gctcatccgg atggcggtag aaactgggaa     480
ggtttctcac cagatccagc cctcaccggt gtactttttg cggagacgat taagggtatt     540
caagatgctg gtgtcattgc gacagctaag cattatatca tgaacgaaca agagcatttc     600
cgccaacaac ccgaggctgc gggttacgga ttcaacgtaa gcgacagttt gagttccaac     660
gttgatgaca agactatgca tgaattgtac ctctggccct cgcggatgc agtacgcgct      720
ggagtcggtg ctgtcatgtg ctcttacaac caaatcaaca cagctacgg ttgcgagaat      780
agcgaaactc tgaacaagct tttgaaggcg gagcttggtt ccaaggctt cgtcatgagt      840
gattggaccc tcatcacag cggcgtaggc gctgctttag caggtctgga tatgtcgatg      900
cccggtgatg ttaccttcga gtggtacg tctttctggg gtgcaaactt gacggtcggt       960
gtccttaacg gtacaatccc ccaatggcgt gttgatgaca tggctgtccg tatcatggcc    1020
gcttattaca aggttggccg cgacaccaaa tacacccctc ccaacttcag ctcgtggacc    1080
agggacgaat atggtttcgc gcataaccat gtttcggaag tgcttacga gagggtcaac    1140
gaattcgtgg acgtgcaacg cgatcatgcc gacctaatcc gtcgcatcgg cgcgcagagc    1200
actgttctgc tgaagaacaa gggtgccttg cccttgagcc gcaaggaaaa gctggtcgcc    1260
cttctgggag aggatgcggg ttccaactcg tggggcgcta acggctgtga tgaccgtggt    1320
tgcgataacg gtaccttgc catggcctgg ggtagcggta ctgcgaattt cccatacctc    1380
gtgacaccag agcaggcgat tcagaacgaa gttcttcagg gccgtggtaa tgtcttcgcc    1440
gtgaccgaca gttgggcgct cgacaagatc gctgcggctg cccgccaggc cagcgtatct    1500
ctcgtgttcg tcaactccga ctcaggagaa ggctatctta gtgtggatgg aaatgagggc    1560
gatcgtaaca acatcactct gtggaagaac ggcgacaatg tggtcaagac cgcagcgaat    1620
```

```
aactgtaaca acaccgttgt catcatccac tccgtcggac cagttttgat cgatgaatgg    1680
tatgaccacc ccaatgtcac tggtattctc tgggctggtc tgccaggcca ggagtctggt    1740
aactccattg ccgatgtgct gtacggtcgt gtcaaccctg cgccaagtc tcctttcact     1800
tggggcaaga cccgggagtc gtatggttct cccttggtca aggatgccaa caatggcaac    1860
ggagcgcccc agtctgattt cacccagggt gttttcatcg attaccgcca tttcgataag    1920
ttcaatgaga ccctatcta cgagtttggc tacggcttga gctacaccac cttcgagctc     1980
tccgacctcc atgttcagcc cctgaacgcg tcccgataca ctcccaccag tggcatgact    2040
gaagctgcaa agaactttgg tgaaattggc gatgcgtcgg agtacgtgta tccggagggg    2100
ctggaaagga tccatgagtt tatctatccc tggatcaact ctaccgacct gaaggcatcg    2160
tctgacgatt ctaactacgg ctgggaagac tccaagtata ttcccgaagg cgccacggat    2220
gggtctgccc agccccgttt gccgctagt ggtggtgccg gaggaaaccc cggtctgtac     2280
gaggatcttt tccgcgtctc tgtgaaggtc aagaacacgg gcaatgtcgc cggtgatgaa    2340
gttcctcagc tgtacgtttc cctaggcggc ccgaatgagc ccaaggtggt actgcgcaag    2400
tttgagcgta ttcacttggc cccttcgcag gaggccgtgt ggacaacgac ccttacccgt    2460
cgtgaccttg caaactggga cgtttcggct caggactgga ccgtcactcc ttaccccaag    2520
acgatctacg ttggaaactc ctcacggaaa ctgccgctcc aggcctcgct gcctaaggcc    2580
cagtaa                                                              2586

<210> SEQ ID NO 6
<211> LENGTH: 2891
<212> TYPE: DNA
<213> ORGANISM: Aspergillus oryzae var. Brunneus
<400> SEQUENCE: 6
atgaagcttg gttggatcga ggtggccgca ttggcggctg cctcagtagt cagtgccaag      60
gtatgcttca gcatctcata cggtgctatt cgactcaatt gaatcagctt tttaacaatt     120
tttactctga ataggatgat ctcgcgtact cccctccttt ctacccttcc ccatgggcag     180
atggtcaggg tgaatgggcg gaagtataca aacgcgctgt agacatagtt tcccagatga    240
cgttgacaga gaaagtcaac ttaacgactg gaacagggta agcttgcgta tgccttagcg     300
tgtctgaagc tcgattagct aaagtacttc agatggcaac tagagaggtg tgttggacaa     360
actggcagtg ttcccaggta agtagatttt cacatgactt tatactctta cggaaggctg    420
attgttgtga atatagactc aacatcccca gcttgtgttt gcaggatagt cctcttggta     480
ttcgtttctg tacgtgtggc ttttatttcc ctttccttcc taacatgttg ctaacagtag    540
acgcgcagcg gactacaatt cagctttccc tgcgggtgtt aatgtcgctg ccacctggga    600
caagacgctc gcctaccttc gtggtcaggc aatgggtgag gagttcagtg ataagggtat    660
tgacgttcag ctgggtcctg ctgctggccc tctcggtgct catccggatg gcggtagaaa    720
ctgggaaggt ttctcaccag atccagccct caccggtgta cttttttgcgg agacgattaa    780
gggtattcaa gatgctggtg tcattgcgac agctaagcat tatatcatga cgaacaaga     840
gcatttccgc caacaacccg aggctgcggg ttacggattc aacgtaagcg acagtttgag    900
ttccaacgtt gatgacaaga ctatgcatga attgtacctc tggcccttcg cggatgcagt    960
acgcgctgga gtcggtgctg tcatgtgctc ttacaaccaa atcaacaaca gctacggttg   1020
cgagaatagc gaaactctga caagctttt gaaggcggag cttggtttcc aaggcttcgt    1080
catgagtgat tggaccgctc atcacagcgg cgtaggcgct gctttagcag gtctggatat   1140
```

```
gtcgatgccc ggtgatgtta ccttcgatag tggtacgtct ttctggggtg caaacttgac    1200
ggtcggtgtc cttaacggta caatccccca atggcgtgtt gatgacatgg ctgtccgtat    1260
catggccgct tattacaagg ttggccgcga caccaaatac acccctccca acttcagctc    1320
gtggaccagg gacgaaatat ggtttcgcgca taaccatgtt tcggaaggtg cttacgagag    1380
ggtcaacgaa ttcgtggacg tgcaacgcga tcatgccgac ctaatccgtc gcatcggcgc    1440
gcagagcact gttctgctga agaacaaggg tgccttgccc ttgagccgca aggaaaagct    1500
ggtcgccctt ctgggagagg atgcgggttc caactcgtgg ggcgctaacg ctgtgatga    1560 ccgtggttgc gataacggta cccttgccat ggcctgggt agcggtactg cgaatttccc    1620
atacctcgtg acaccagagc aggcgattca gaacgaagtt cttcagggcc gtggtaatgt    1680
cttcgccgtg accgacagtt gggcgctcga caagatcgct gcggctgccc gccaggccag    1740
cgtatctctc gtgttcgtca actccgactc aggagaaggc tatcttagtg tggatggaaa    1800
tgagggcgat cgtaacaaca tcactctgtg gaagaacggc gacaatgtgg tcaagaccgc    1860
agcgaataac tgtaacaaca ccgttgtcat catccactcc gtcggaccag ttttgatcga    1920
tgaatggtat gaccacccca atgtcactgg tattctctgg gctggtctgc aggccagga    1980 gtctggtaac tccattgccg atgtgctgta cggtcgtgtc aaccctggcg ccaagtctcc    2040
tttcacttgg ggcaagaccc gggagtcgta tggttctccc ttggtcaagg atgccaacaa    2100
tggcaacgga gcgccccagt ctgatttcac ccagggtgtt ttcatcgatt accgccattt    2160
cgataagttc aatgagaccc ctatctacga gtttggctac ggcttgagct acaccacctt    2220
cgagctctcc gacctccatg ttcagcccct gaacgcgtcc cgatacactc ccaccagtgg    2280
catgactgaa gctgcaaaga ctttggtga aattggcgat cgtcggagt acgtgtatcc    2340 ggaggggctg gaaaggatcc atgagtttat ctatccctgg atcaactcta ccgacctgaa    2400
ggcatcgtct gacgattcta actacggctg gaagactcc aagtatattc ccgaaggcgc    2460
cacggatggg tctgcccagc cccgtttgcc cgctagtggt ggtgccggag gaaacccccgg    2520 tctgtacgag gatctttttcc gcgtctctgt gaaggtcaag aacacgggca atgtcgccgg    2580
tgatgaagtt cctcagctgg taagttgacc tgattgggtg atgtgtaata atttcaatgc    2640 taacttttc tgtgtagtac gtttccctag gcggcccgaa tgagcccaag gtggtactgc    2700
gcaagtttga gcgtattcac ttggccccctt cgcaggaggc cgtgtggaca acgacccctta    2760 cccgtcgtga ccttgcaaac tgggacgttt cggctcagga ctggaccgtc actccttacc    2820
ccaagacgat ctacgttgga aactcctcac ggaaactgcc gctccaggcc tcgctgccta    2880
aggcccagta a                                                        2891
```

<210> SEQ ID NO 7
<211> LENGTH: 861
<212> TYPE: PRT
<213> ORGANISM: Aspergillus oryzae var. Brunneus

<400> SEQUENCE: 7

Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr

```
                50                  55                  60
Thr Gly Thr Gly Trp Gln Leu Glu Arg Cys Val Gly Gln Thr Gly Ser
 65                  70                  75                  80

Val Pro Arg Leu Asn Ile Pro Ser Leu Cys Leu Gln Asp Ser Pro Leu
                 85                  90                  95

Gly Ile Arg Phe Ser Asp Tyr Asn Ser Ala Phe Pro Ala Gly Val Asn
                100                 105                 110

Val Ala Ala Thr Trp Asp Lys Thr Leu Ala Tyr Leu Arg Gly Gln Ala
                115                 120                 125

Met Gly Glu Glu Phe Ser Asp Lys Gly Ile Asp Val Gln Leu Gly Pro
130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
                180                 185                 190

Ile Met Asn Glu Gln Glu His Phe Arg Gln Gln Pro Glu Ala Ala Gly
                195                 200                 205

Tyr Gly Phe Asn Val Ser Asp Ser Leu Ser Ser Asn Val Asp Asp Lys
210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
                260                 265                 270

Gly Phe Gln Gly Phe Val Met Ser Asp Trp Thr Ala His His Ser Gly
                275                 280                 285

Val Gly Ala Ala Leu Ala Gly Leu Asp Met Ser Met Pro Gly Asp Val
                290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Met Ala Val
                325                 330                 335

Arg Ile Met Ala Ala Tyr Tyr Lys Val Gly Arg Asp Thr Lys Tyr Thr
                340                 345                 350

Pro Pro Asn Phe Ser Ser Trp Thr Arg Asp Glu Tyr Gly Phe Ala His
                355                 360                 365

Asn His Val Ser Glu Gly Ala Tyr Glu Arg Val Asn Glu Phe Val Asp
                370                 375                 380

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
                405                 410                 415

Lys Leu Val Ala Leu Leu Gly Glu Asp Ala Gly Ser Asn Ser Trp Gly
                420                 425                 430

Ala Asn Gly Cys Asp Asp Arg Gly Cys Asp Asn Gly Thr Leu Ala Met
                435                 440                 445

Ala Trp Gly Ser Gly Thr Ala Asn Phe Pro Tyr Leu Val Thr Pro Glu
                450                 455                 460

Gln Ala Ile Gln Asn Glu Val Leu Gln Gly Arg Gly Asn Val Phe Ala
465                 470                 475                 480
```

-continued

```
Val Thr Asp Ser Trp Ala Leu Asp Lys Ile Ala Ala Ala Arg Gln
            485                 490                 495

Ala Ser Val Ser Leu Val Phe Val Asn Ser Asp Ser Gly Glu Gly Tyr
            500                 505                 510

Leu Ser Val Asp Gly Asn Glu Gly Asp Arg Asn Asn Ile Thr Leu Trp
            515                 520                 525

Lys Asn Gly Asp Asn Val Lys Thr Ala Ala Asn Asn Cys Asn Asn
    530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
                565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
            595                 600                 605

Gly Ser Pro Leu Val Lys Asp Ala Asn Asn Gly Asn Gly Ala Pro Gln
            610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
                645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
            675                 680                 685

Ile Gly Asp Ala Ser Glu Tyr Val Tyr Pro Glu Gly Leu Glu Arg Ile
    690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
                725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
            755                 760                 765

Lys Val Lys Asn Thr Gly Asn Val Ala Gly Asp Glu Val Pro Gln Leu
    770                 775                 780

Tyr Val Ser Leu Gly Gly Pro Asn Glu Pro Lys Val Val Leu Arg Lys
785                 790                 795                 800

Phe Glu Arg Ile His Leu Ala Pro Ser Gln Glu Ala Val Trp Thr Thr
                805                 810                 815

Thr Leu Thr Arg Arg Asp Leu Ala Asn Trp Asp Val Ser Ala Gln Asp
            820                 825                 830

Trp Thr Val Thr Pro Tyr Pro Lys Thr Ile Tyr Val Gly Asn Ser Ser
            835                 840                 845

Arg Lys Leu Pro Leu Gln Ala Ser Leu Pro Lys Ala Gln
    850                 855                 860

<210> SEQ ID NO 8
<211> LENGTH: 842
<212> TYPE: PRT
<213> ORGANISM: Aspergillus oryzae var. Brunneus
```

<400> SEQUENCE: 8

```
Lys Asp Asp Leu Ala Tyr Ser Pro Pro Phe Tyr Pro Ser Pro Trp Ala
1               5                   10                  15

Asp Gly Gln Gly Glu Trp Ala Glu Val Tyr Lys Arg Ala Val Asp Ile
            20                  25                  30

Val Ser Gln Met Thr Leu Thr Glu Lys Val Asn Leu Thr Gly Thr
        35                  40                  45

Gly Trp Gln Leu Glu Arg Cys Val Gly Gln Thr Gly Ser Val Pro Arg
    50                  55                  60

Leu Asn Ile Pro Ser Leu Cys Leu Gln Asp Ser Pro Leu Gly Ile Arg
65                  70                  75                  80

Phe Ser Asp Tyr Asn Ser Ala Phe Pro Ala Gly Val Asn Val Ala Ala
                85                  90                  95

Thr Trp Asp Lys Thr Leu Ala Tyr Leu Arg Gly Gln Ala Met Gly Glu
            100                 105                 110

Glu Phe Ser Asp Lys Gly Ile Asp Val Gln Leu Gly Pro Ala Ala Gly
        115                 120                 125

Pro Leu Gly Ala His Pro Asp Gly Gly Arg Asn Trp Glu Gly Phe Ser
    130                 135                 140

Pro Asp Pro Ala Leu Thr Gly Val Leu Phe Ala Glu Thr Ile Lys Gly
145                 150                 155                 160

Ile Gln Asp Ala Gly Val Ile Ala Thr Ala Lys His Tyr Ile Met Asn
                165                 170                 175

Glu Gln Glu His Phe Arg Gln Gln Pro Glu Ala Ala Gly Tyr Gly Phe
            180                 185                 190

Asn Val Ser Asp Ser Leu Ser Ser Asn Val Asp Asp Lys Thr Met His
        195                 200                 205

Glu Leu Tyr Leu Trp Pro Phe Ala Asp Ala Val Arg Ala Gly Val Gly
    210                 215                 220

Ala Val Met Cys Ser Tyr Asn Gln Ile Asn Asn Ser Tyr Gly Cys Glu
225                 230                 235                 240

Asn Ser Glu Thr Leu Asn Lys Leu Leu Lys Ala Glu Leu Gly Phe Gln
                245                 250                 255

Gly Phe Val Met Ser Asp Trp Thr Ala His His Ser Gly Val Gly Ala
            260                 265                 270

Ala Leu Ala Gly Leu Asp Met Ser Met Pro Gly Asp Val Thr Phe Asp
        275                 280                 285

Ser Gly Thr Ser Phe Trp Gly Ala Asn Leu Thr Val Gly Val Leu Asn
    290                 295                 300

Gly Thr Ile Pro Gln Trp Arg Val Asp Asp Met Ala Val Arg Ile Met
305                 310                 315                 320

Ala Ala Tyr Tyr Lys Val Gly Arg Asp Thr Lys Tyr Thr Pro Pro Asn
                325                 330                 335

Phe Ser Ser Trp Thr Arg Asp Glu Tyr Gly Phe Ala His Asn His Val
            340                 345                 350

Ser Glu Gly Ala Tyr Glu Arg Val Asn Glu Phe Val Asp Val Gln Arg
        355                 360                 365

Asp His Ala Asp Leu Ile Arg Arg Ile Gly Ala Gln Ser Thr Val Leu
    370                 375                 380

Leu Lys Asn Lys Gly Ala Leu Pro Leu Ser Arg Lys Glu Lys Leu Val
385                 390                 395                 400

Ala Leu Leu Gly Glu Asp Ala Gly Ser Asn Ser Trp Gly Ala Asn Gly
                405                 410                 415
```

-continued

```
Cys Asp Asp Arg Gly Cys Asp Asn Gly Thr Leu Ala Met Ala Trp Gly
            420                 425                 430
Ser Gly Thr Ala Asn Phe Pro Tyr Leu Val Thr Pro Glu Gln Ala Ile
        435                 440                 445
Gln Asn Glu Val Leu Gln Gly Arg Gly Asn Val Phe Ala Val Thr Asp
450                 455                 460
Ser Trp Ala Leu Asp Lys Ile Ala Ala Ala Arg Gln Ala Ser Val
465                 470                 475                 480
Ser Leu Val Phe Val Asn Ser Asp Ser Gly Glu Gly Tyr Leu Ser Val
                485                 490                 495
Asp Gly Asn Glu Gly Asp Arg Asn Asn Ile Thr Leu Trp Lys Asn Gly
            500                 505                 510
Asp Asn Val Val Lys Thr Ala Ala Asn Cys Asn Asn Thr Val Val
        515                 520                 525
Ile Ile His Ser Val Gly Pro Val Leu Ile Asp Glu Trp Tyr Asp His
530                 535                 540
Pro Asn Val Thr Gly Ile Leu Trp Ala Gly Leu Pro Gly Gln Glu Ser
545                 550                 555                 560
Gly Asn Ser Ile Ala Asp Val Leu Tyr Gly Arg Val Asn Pro Gly Ala
                565                 570                 575
Lys Ser Pro Phe Thr Trp Gly Lys Thr Arg Glu Ser Tyr Gly Ser Pro
            580                 585                 590
Leu Val Lys Asp Ala Asn Asn Gly Asn Gly Ala Pro Gln Ser Asp Phe
        595                 600                 605
Thr Gln Gly Val Phe Ile Asp Tyr Arg His Phe Asp Lys Phe Asn Glu
610                 615                 620
Thr Pro Ile Tyr Glu Phe Gly Tyr Gly Leu Ser Tyr Thr Thr Phe Glu
625                 630                 635                 640
Leu Ser Asp Leu His Val Gln Pro Leu Asn Ala Ser Arg Tyr Thr Pro
                645                 650                 655
Thr Ser Gly Met Thr Glu Ala Ala Lys Asn Phe Gly Glu Ile Gly Asp
            660                 665                 670
Ala Ser Glu Tyr Val Tyr Pro Glu Gly Leu Glu Arg Ile His Glu Phe
        675                 680                 685
Ile Tyr Pro Trp Ile Asn Ser Thr Asp Leu Lys Ala Ser Ser Asp Asp
690                 695                 700
Ser Asn Tyr Gly Trp Glu Asp Ser Lys Tyr Ile Pro Glu Gly Ala Thr
705                 710                 715                 720
Asp Gly Ser Ala Gln Pro Arg Leu Pro Ala Ser Gly Gly Ala Gly Gly
                725                 730                 735
Asn Pro Gly Leu Tyr Glu Asp Leu Phe Arg Val Ser Val Lys Val Lys
            740                 745                 750
Asn Thr Gly Asn Val Ala Gly Asp Glu Val Pro Gln Leu Tyr Val Ser
        755                 760                 765
Leu Gly Gly Pro Asn Glu Pro Lys Val Val Leu Arg Lys Phe Glu Arg
770                 775                 780
Ile His Leu Ala Pro Ser Gln Glu Ala Val Trp Thr Thr Thr Leu Thr
785                 790                 795                 800
Arg Arg Asp Leu Ala Asn Trp Asp Val Ser Ala Gln Asp Trp Thr Val
                805                 810                 815
Thr Pro Tyr Pro Lys Thr Ile Tyr Val Gly Asn Ser Ser Arg Lys Leu
            820                 825                 830
```

Pro Leu Gln Ala Ser Leu Pro Lys Ala Gln
        835                 840

<210> SEQ ID NO 9
<211> LENGTH: 29
<212> TYPE: DNA
<213> ORGANISM: Artificial
<220> FEATURE:
<223> OTHER INFORMATION: Synthetic DNA

<400> SEQUENCE: 9
agatctatga agcttggttg gatcgaggt                                    29

<210> SEQ ID NO 10
<211> LENGTH: 27
<212> TYPE: DNA
<213> ORGANISM: Artificial
<220> FEATURE:
<223> OTHER INFORMATION: Synthetic DNA

<400> SEQUENCE: 10
gtcgacttac tgggccttag gcagcga                                      27

<210> SEQ ID NO 11
<211> LENGTH: 33
<212> TYPE: DNA
<213> ORGANISM: Artificial
<220> FEATURE:
<223> OTHER INFORMATION: Synthetic DNA

<400> SEQUENCE: 11
gcggccgcat ggtttccggt gtctttacga agg                               33

<210> SEQ ID NO 12
<211> LENGTH: 33
<212> TYPE: DNA
<213> ORGANISM: Artificial
<220> FEATURE:
<223> OTHER INFORMATION: Synthetic DNA

<400> SEQUENCE: 12
ggatcctcac tgcacataga aagtagcatt gcc                               33

<210> SEQ ID NO 13
<211> LENGTH: 29
<212> TYPE: DNA
<213> ORGANISM: Artificial
<220> FEATURE:
<223> OTHER INFORMATION: Synthetic DNA

<400> SEQUENCE: 13
tactattagc tgaattgcca ctgctatcg                                    29

<210> SEQ ID NO 14
<211> LENGTH: 27
<212> TYPE: DNA
<213> ORGANISM: Artificial
<220> FEATURE:
<223> OTHER INFORMATION: Synthetic DNA

<400> SEQUENCE: 14
tctacaaccg ctaaatgttt ttgttcg                                      27

<210> SEQ ID NO 15
<211> LENGTH: 19
<212> TYPE: DNA

<213> ORGANISM: Artificial
<220> FEATURE:
<223> OTHER INFORMATION: Synthetic DNA

<400> SEQUENCE: 15
aattaattaa gagctagcg                                                  19

<210> SEQ ID NO 16
<211> LENGTH: 19
<212> TYPE: DNA
<213> ORGANISM: Artificial
<220> FEATURE:
<223> OTHER INFORMATION: Synthetic DNA

<400> SEQUENCE: 16
ttaattctcg atcgcttaa                                                  19

<210> SEQ ID NO 17
<211> LENGTH: 31
<212> TYPE: DNA
<213> ORGANISM: Artificial
<220> FEATURE:
<223> OTHER INFORMATION: Synthetic DNA

<400> SEQUENCE: 17
taagatctaa ggatgatctc gcgtactccc c                                    31

<210> SEQ ID NO 18
<211> LENGTH: 27
<212> TYPE: DNA
<213> ORGANISM: Artificial
<220> FEATURE:
<223> OTHER INFORMATION: Synthetic DNA

<400> SEQUENCE: 18
gtcgacttac tgggccttag gcagcga                                         27

<210> SEQ ID NO 19
<211> LENGTH: 33
<212> TYPE: DNA
<213> ORGANISM: Artificial
<220> FEATURE:
<223> OTHER INFORMATION: Synthetic DNA

<400> SEQUENCE: 19
aaggatccca agatgagaag cctcgctaca agg                                  33

<210> SEQ ID NO 20
<211> LENGTH: 35
<212> TYPE: DNA
<213> ORGANISM: Artificial
<220> FEATURE:
<223> OTHER INFORMATION: Synthetic DNA

<400> SEQUENCE: 20
gggtcgactc actgcacata gaaagtagca ttgcc                                35

<210> SEQ ID NO 21
<211> LENGTH: 55
<212> TYPE: DNA
<213> ORGANISM: Artificial
<220> FEATURE:
<223> OTHER INFORMATION: Synthetic DNA

<400> SEQUENCE: 21
taaatgttta aatctgttgt ttattcaatt ttagccgctt ctttggccaa tgcag          55

-continued

<210> SEQ ID NO 22
<211> LENGTH: 61
<212> TYPE: DNA
<213> ORGANISM: Artificial
<220> FEATURE:
<223> OTHER INFORMATION: Synthetic DNA

<400> SEQUENCE: 22
ctagctgcat tggccaaaga agcggctaaa attgaataaa caacagattt aaacatttaa    60
t                                                                    61

<210> SEQ ID NO 23
<211> LENGTH: 61
<212> TYPE: DNA
<213> ORGANISM: Artificial
<220> FEATURE:
<223> OTHER INFORMATION: Synthetic DNA

<400> SEQUENCE: 23
taaatgcttt tgcaagcttt cctttccctt ttggctggtt ttgcagccaa aatatctgca    60
g                                                                    61

<210> SEQ ID NO 24
<211> LENGTH: 61
<212> TYPE: DNA
<213> ORGANISM: Artificial
<220> FEATURE:
<223> OTHER INFORMATION: Synthetic DNA

<400> SEQUENCE: 24
taaatgagat ttccttcaat ttttactgca gttttattcg cagcatcctc cgcattagct    60
g                                                                    61

<210> SEQ ID NO 25
<211> LENGTH: 61
<212> TYPE: DNA
<213> ORGANISM: Artificial
<220> FEATURE:
<223> OTHER INFORMATION: Synthetic DNA

<400> SEQUENCE: 25
taaatgagat ttccttcaat ttttactgca gttttattcg cagcatcctc cgcattagct    60
g                                                                    61

<210> SEQ ID NO 26
<211> LENGTH: 67
<212> TYPE: DNA
<213> ORGANISM: Artificial
<220> FEATURE:
<223> OTHER INFORMATION: Synthetic DNA

<400> SEQUENCE: 26
ctagcagcta atgcggagga tgctgcgaat aaaactgcag taaaaattga aggaaatctc    60
atttaat                                                              67

<210> SEQ ID NO 27
<211> LENGTH: 57
<212> TYPE: DNA
<213> ORGANISM: Aspergillus oryzae var. Brunneus
<220> FEATURE:
<221> NAME/KEY: CDS
<222> LOCATION: (1)..(57)

```
<400> SEQUENCE: 27 atg aag ctt ggt tgg atc gag gtg gcc gca ttg gcg gct gcc tca gta       48
Met Lys Leu Gly Trp Ile Glu Val Ala Ala Leu Ala Ala Ala Ser Val
1               5                   10                  15 gtc agt gcc                                                           57
Val Ser Ala <210> SEQ ID NO 28
<211> LENGTH: 19
<212> TYPE: PRT
<213> ORGANISM: Aspergillus oryzae var. Brunneus

<400> SEQUENCE: 28

Met Lys Leu Gly Trp Ile Glu Val Ala Ala Leu Ala Ala Ala Ser Val
1               5                   10                  15

Val Ser Ala

<210> SEQ ID NO 29
<211> LENGTH: 66
<212> TYPE: DNA
<213> ORGANISM: Aspergillus oryzae var. Brunneus
<220> FEATURE:
<221> NAME/KEY: CDS
<222> LOCATION: (1)..(66)

<400> SEQUENCE: 29 atg gtt tcc ggt gtc ttt acg aag ggg gtt ctg ctc ctg ggc ctc ttg       48
Met Val Ser Gly Val Phe Thr Lys Gly Val Leu Leu Leu Gly Leu Leu
1               5                   10                  15 tcg ggt ctg gct ctt ggt                                               66
Ser Gly Leu Ala Leu Gly
            20

<210> SEQ ID NO 30
<211> LENGTH: 22
<212> TYPE: PRT
<213> ORGANISM: Aspergillus oryzae var. Brunneus

<400> SEQUENCE: 30

Met Val Ser Gly Val Phe Thr Lys Gly Val Leu Leu Leu Gly Leu Leu
1               5                   10                  15

Ser Gly Leu Ala Leu Gly
            20

<210> SEQ ID NO 31
<211> LENGTH: 57
<212> TYPE: DNA
<213> ORGANISM: Saccharomyces cerevisiae
<220> FEATURE:
<221> NAME/KEY: CDS
<222> LOCATION: (1)..(57)

<400> SEQUENCE: 31 atg aga ttt cct tca att ttt act gca gtt tta ttc gca gca tcc tcc       48
Met Arg Phe Pro Ser Ile Phe Thr Ala Val Leu Phe Ala Ala Ser Ser
1               5                   10                  15 gca tta gct                                                           57
Ala Leu Ala <210> SEQ ID NO 32
<211> LENGTH: 19
<212> TYPE: PRT
<213> ORGANISM: Saccharomyces cerevisiae
```

```
<400> SEQUENCE: 32

Met Arg Phe Pro Ser Ile Phe Thr Ala Val Leu Phe Ala Ala Ser Ser
1               5                   10                  15

Ala Leu Ala

<210> SEQ ID NO 33
<211> LENGTH: 51
<212> TYPE: DNA
<213> ORGANISM: Saccharomyces cerevisiae
<220> FEATURE:
<221> NAME/KEY: CDS
<222> LOCATION: (1)..(51)

<400> SEQUENCE: 33 atg ttt aaa tct gtt gtt tat tca att tta gcc gct tct ttg gcc aat      48
Met Phe Lys Ser Val Val Tyr Ser Ile Leu Ala Ala Ser Leu Ala Asn
1               5                   10                  15 gca                                                                  51
Ala

<210> SEQ ID NO 34
<211> LENGTH: 17
<212> TYPE: PRT
<213> ORGANISM: Saccharomyces cerevisiae

<400> SEQUENCE: 34

Met Phe Lys Ser Val Val Tyr Ser Ile Leu Ala Ala Ser Leu Ala Asn
1               5                   10                  15

Ala

<210> SEQ ID NO 35
<211> LENGTH: 57
<212> TYPE: DNA
<213> ORGANISM: Saccharomyces cerevisiae
<220> FEATURE:
<221> NAME/KEY: CDS
<222> LOCATION: (1)..(57)

<400> SEQUENCE: 35 atg ctt ttg caa gct ttc ctt ttc ctt ttg gct ggt ttt gca gcc aaa      48
Met Leu Leu Gln Ala Phe Leu Phe Leu Leu Ala Gly Phe Ala Ala Lys
1               5                   10                  15 ata tct gca                                                          57
Ile Ser Ala <210> SEQ ID NO 36
<211> LENGTH: 19
<212> TYPE: PRT
<213> ORGANISM: Saccharomyces cerevisiae

<400> SEQUENCE: 36

Met Leu Leu Gln Ala Phe Leu Phe Leu Leu Ala Gly Phe Ala Ala Lys
1               5                   10                  15

Ile Ser Ala
```

METHOD FOR PRODUCING STEVIOL AND STEVIOL GLYCOSIDE USING AOBGL3 HOMOLOG

SEQUENCE LISTING

The instant application contains a Sequence Listing which has been filed electronically in ASCII format and is hereby incorporated by reference in its entirety. Said ASCII copy, created on Apr. 26, 2019, is named P54597_SL.txt and is 50,371 bytes in size.

TECHNICAL FIELD

The present invention relates to a method for producing a steviol glycoside and steviol.

BACKGROUND ART

The leaves of *Stevia rebaudiana* of the Asteraceae family contain a secondary metabolite called "steviol" which is a kind of diterpenoid. Steviol glycosides, which are products of the addition of sugars to steviol, include those having sweetness about 300 times higher than that of table sugar. Such steviol glycosides are used as non-caloric sweeteners in the food industry.

Obesity is becoming more of a serious social issue on an international scale, and non-caloric sweeteners are increasingly demanded from the viewpoint of promotion of health and reduction of medical cost. Currently, aspartame and acesulfame potassium, which are artificially-synthesized amino acid derivatives, are used as artificial sweeteners. However, naturally-occurring non-caloric sweeteners such as steviol glycosides are expected to be safer and gain more public acceptance.

Among steviol glycosides, stevioside is a compound in which three glucose units are added to steviol, and is contained in the largest amount in the leaves of common *Stevia rebaudiana*. Stevioside has a degree of sweetness about 300 times higher than that of sucrose, but has slightly bitter taste. Rebaudioside A, which is another steviol glycoside, is a compound in which four glucose units are added to steviol, and has a degree of sweetness about 400 times higher than that of sucrose. Stevioside and rebaudioside A are primary substances responsible for the sweetness of *Stevia rebaudiana*. There are also known glycosides such as rebaudioside D in which five glucose units are added to steviol and rebaudioside M in which six glucose units are added to steviol. It is also known that *Rubus suavissimus* contains rubusoside in which one glucose unit is added at each of the 13 and 19 positions of steviol and that this rubusoside is a primary sweet component of *Rubus suavissimus*. In addition to the above glycosides, glycosides considered to be reaction intermediates and analogs differing in the type of sugar are known to exist (FIG. 1).

Meanwhile, steviol is known to have, for example, improving effect on cognitive function.

If an enzyme acting only on a specific glycoside bond in steviol glycosides can be used, production of a specific glycoside or elimination of an unnecessary glycoside will become possible. This will bring a lot of merits such as facilitating the improvement in taste of *Stevia rebaudiana* extracts or the purification of a specific steviol glycoside.

An enzyme activity to hydrolyze steviol glycosides has been reported to be observed in some organism species. In particular, concerning the production of steviol glycoside-hydrolyzing enzymes by filamentous fungi of the genus *Aspergillus*, it has been reported that raw soy sauce has an activity to hydrolyze stevioside into rubusoside (Non Patent Literature 1) and that a pectinase enzyme agent, hesperidinase enzyme agent, and takadiastase enzyme agent have an activity to hydrolyze stevioside into steviol (Non Patent Literatures 2 to 4). A method has also been reported in which steviol is produced from stevioside by the combined use of a pectinase enzyme agent derived from filamentous fungi of the genus *Aspergillus* and an enzyme agent derived from *Helix pomatia* (Patent Literature 1). Viscozyme L (novozyme), an enzyme agent derived from *Aspergillus aculeatus*, has been described to have an activity to hydrolyze stevioside into rubusoside and then into steviol monglycosyl ester (Non Patent Literature 5). Additionally, an extract obtained from *Aspergillus aculeatus* by solid culture has been described to have an activity to convert stevioside into steviol (Non Patent Literature 6).

As stated above, filamentous fungi of the genus *Aspergillus*, including koji mold, have been suggested to have an enzyme gene having steviol glycoside-hydrolyzing activity. However, there has been no report of any gene or enzyme responsible for enzyme activity.

It has been reported that the β-glucosidase of the glycoside hydrolase (GH) family 3 encoded by the AO090009000356 gene of koji mold hydrolyzes disaccharides with a β-glucoside bond (Non Patent Literature 7). Specifically, its specificity for hydrolysis is the highest for laminaribiose with a β-1,3 linkage, followed by β-gentiobiose with a β-1,6 linkage, cellobiose with a β-1,4 linkage, and sophorose with a β-1,2 linkage. However, there has been no report on whether the β-glucosidase has an activity to hydrolyze terpene glycosides typified by steviol glycosides.

Some other organisms have also been reported to have an activity to hydrolyze steviol glycosides. For example, it has been disclosed that bacteria of the genus *Clavibacter* have an enzyme that decomposes the glucosyl ester bond at the 19 position of rubusoside but does not decompose the glucoside bond at the 13 position (Patent Literature 2). Additionally, it has been reported that *Flavobacterium johnsoniae*-derived β-glucosidase has an activity to decompose steviol glycosides (an activity to hydrolyze the β-glucoside bond at the 13 position and the glucosyl ester bond at the 19 position).

Although these have been found to have an activity to hydrolyze steviol glycosides, the gene responsible for this activity has not been identified.

Moreover, koji mold contains a large number of genes considered to encode GH3 family or GH5 family enzymes having β-glucosidase-like activity, and thus, even if an enzyme activity can be detected, it is not easy to determine which gene is responsible for the activity.

CITATION LIST

Patent Literature

Patent Literature 1: National Publication of International Patent Application No. 2013-516963
Patent Literature 2: Japanese Patent Laid-Open No. 10-276775
Patent Literature 3: Japanese Patent Laid-Open No. 10-276775

Non Patent Literature

Non Patent Literature 1: Journal of the Japanese Society for Food Science and Technology, vol. 37, No. 5, 369-374 (1990)

Non Patent Literature 2: Phytochemistry, 6, 1107 (1967)
Non Patent Literature 3: Journal of the Pharmaceutical Society of Japan, 95, 1507 (1975)
Non Patent Literature 4: Journal of the Chemical Society of Japan, 1981, 726 (1981)
Non Patent Literature 5: J. Agric. Food Chem., 60, 6210-6216(2012)
Non Patent Literature 6: Wei Sheng Wu Xue Bao, 54(1), 62-68(2014)
Non Patent Literature 7: Biochim Biophys Acta., 1764 972-978 (2006)

SUMMARY OF INVENTION

Technical Problem

Under the foregoing circumstances, there is a need for a novel method for producing Steviol glycosides and Steviol.

Solution to Problem

The present inventors conducted extensive research to solve the aforementioned problem, and found that a koji mold-derived glycoside hydrolase homolog protein encoded by AOBGL3 gene has an activity to hydrolyze steviol glycosides. That is, the present inventors have found that, for example, the protein has an activity to cleave a monoglucoside and/or monoglucosyl ester of a steviol glycoside, thus completing the present invention. Additionally, the present inventors have succeeded in producing a steviol glycoside and/or steviol by further expressing another koji mold-derived glycosidase homolog protein encoded by AOBGL1 gene, thus completing the present invention.

In summary, the present invention is as set forth below.

[1]
A method for preparing a steviol glycoside and/or steviol comprising reacting a protein selected from the group consisting of proteins (a) to (c) shown below with a steviol glycoside having at least one monoglucoside bond and/or monoglucosyl ester bond, thereby cleaving said monoglucoside bond and/or monoglucosyl ester bond:

(a) a protein consisting of the amino acid sequence of SEQ ID NO: 3 or 4;

(b) a protein consisting of an amino acid sequence wherein 1 to 77 amino acids have been deleted, substituted, inserted, and/or added in the amino acid sequence of SEQ ID NO: 3 or 4, and having an activity to cleave a monoglucoside bond and/or monoglucosyl ester bond; and (c) a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside.

[2]
The method according to [1] above, wherein the steviol glycoside having at least one monoglucoside bond and/or monoglucosyl ester bond is selected from rebaudioside A, stevioside, rubusoside, steviolmonoside, and steviol monoglucosyl ester.

[3]
The method according to [2] above, wherein the steviol glycoside having no monoglucoside bond and/or monoglucosyl ester bond is rubusoside.

[4]
A method for producing a steviol glycoside and/or steviol having no monoglucoside bond and/or monoglucosyl ester bond comprising culturing a non-human transformant obtained by introducing a polynucleotide selected from the group consisting of polynucleotides (a) to (e) shown below into a host producing a steviol glycoside having at least one monoglucoside bond and/or monoglucosyl ester bond:

(a) a polynucleotide consisting of the nucleotide sequence of SEQ ID NO: 1;

(b) a polynucleotide encoding a protein consisting of the amino acid sequence of SEQ ID NO: 3 or 4;

(c) a polynucleotide encoding a protein consisting of an amino acid sequence wherein 1 to 77 amino acids have been deleted, substituted, inserted, and/or added in the amino acid sequence of SEQ ID NO: 3 or 4, and having an activity to cleave a monoglucoside bond and/or monoglucosyl ester bond of a steviol glycoside;

(d) a polynucleotide encoding a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside; and (e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to cleave a monoglucoside bond and/or monoglucosyl ester bond of a steviol glycoside.

[5]
The method according to [4] above, wherein the polynucleotide is inserted into an expression vector.

[6]
The method according to [4] or [5] above, wherein the transformant is transformed koji mold, transformed yeast, or a transformed plant.

[7]
A method for preparing a steviol glycoside and/or steviol having no monoglucoside bond and/or monoglucosyl ester bond comprising contacting an enzyme agent derived from a non-human transformed cell obtained by introducing, into a host cell, a polynucleotide selected from the group consisting of polynucleotides (a) to (e) shown below, with a steviol glycoside having at least one monoglucoside bond and/or monoglucosyl ester bond, thereby cleaving said monoglucoside bond and/or monoglucosyl ester bond:

(a) a polynucleotide consisting of the nucleotide sequence of SEQ ID NO: 1;

(b) a polynucleotide encoding a protein consisting of the amino acid sequence of SEQ ID NO: 3 or 4;

(c) a polynucleotide encoding a protein consisting of an amino acid sequence wherein 1 to 77 amino acids have been deleted, substituted, inserted, and/or added in the amino acid sequence of SEQ ID NO: 3 or 4, and having an activity to cleave a monoglucoside bond and/or monoglucosyl ester bond of a steviol glycoside;

(d) a polynucleotide encoding a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside; and (e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to cleave a monoglucoside bond and/or monoglucosyl ester bond of a steviol glycoside.

[8]
The method according to [7] above, wherein the polynucleotide is inserted into an expression vector.

[9]
The method according to [7] or [8] above, wherein the transformed cell is transformed koji mold, a transformed bacterium, or transformed yeast.

[10]
The method according to any one of [7] to [9] above, wherein the steviol glycoside having at least one monoglucoside bond and/or monoglucosyl ester bond is selected from rebaudioside A, stevioside, rubusoside, steviolmonoside, and steviol monoglucosyl ester.

[11]
The method according to [10] above, wherein the steviol glycoside having no monoglucoside bond and/or monoglucosyl ester bond is selected from rebaudioside B and steviolbioside.

[12]
A method for producing a steviol glycoside and/or steviol comprising reacting a protein selected from the group consisting of proteins (a) to (c) shown below, a protein selected from the group consisting of proteins (d) to (f) shown below, and a steviol glycoside having at least one monoglucoside bond and/or monoglucosyl ester bond:

(a) a protein consisting of the amino acid sequence of SEQ ID NO: 3 or 4;

(b) a protein consisting of an amino acid sequence wherein 1 to 77 amino acids have been deleted, substituted, inserted, and/or added in the amino acid sequence of SEQ ID NO: 3 or 4, and having an activity to cleave a monoglucoside bond and/or monoglucosyl ester bond of a steviol glycoside;

(c) a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside;

(d) a protein consisting of the amino acid sequence of SEQ ID NO: 7 or 8;

(e) a protein consisting of an amino acid sequence wherein 1 to 77 amino acids have been deleted, substituted, inserted, and/or added in the amino acid sequence of SEQ ID NO: 7 or 8, and having an activity to cleave an unbranched β-1,2-glucoside bond of a steviol glycoside; and (f) a protein having an amino acid sequence having 90% or more sequence identity to the amino acid sequence of SEQ ID NO: 7 or 8, and having an activity to cleave an unbranched β-1,2-glucoside bond of a steviol glycoside.

[13]
The method according to [12] above, wherein the steviol glycoside having at least one monoglucoside bond and/or monoglucosyl ester bond comprises one or more steviol glycosides selected from rebaudioside A, rebaudioside D, stevioside, rubusoside, steviolmonoside, and steviol monoglucosyl ester.

Advantageous Effects of Invention

According to the present invention, there is provided a novel method for preparing steviol and a steviol glycoside. With the method according to the present invention, a steviol glycoside and/or steviol having no monoglucoside bond and/or monoglucosyl ester bond can be produced. Additionally, a steviol glycoside and/or steviol having no monoglucoside bond and/or monoglucosyl ester bond can be efficiently extracted and purified.

BRIEF DESCRIPTION OF DRAWINGS

FIG. 1 shows the structure of various steviol glycosides.
FIG. 2 shows amino acid sequences and nucleotide sequences of secretory signals, wherein (A) shows MF(ALPHA)1 (YPL187W), (B) shows PHO5 (YBR093C), and (C) shows SUC2 (YIL162W).

DESCRIPTION OF EMBODIMENTS

The present invention will be hereinafter described in detail. The following embodiments are illustrative of the present invention, and are not intended to limit the present invention. The present invention can be carried out in various manners, without departing from the gist of the invention.

Note that all documents, as well as laid-open application publications, patent application publications, and other patent documents cited herein shall be incorporated herein by reference. The present specification incorporates the contents of the specification and the drawings of Japanese Patent Application No. 2015-214256, filed on Oct. 30, 2015, from which the present application claims priority.

"AOBGL3" designates a koji mold-derived β-glucosidase; the cDNA sequence, the genomic DNA sequence, the amino acid sequence, and the amino acid sequence of the mature protein are shown in SEQ ID NO: 1, SEQ ID NO: 2, SEQ ID NO: 3, and SEQ ID NO: 4, respectively.

"AOBGL1" designates a koji mold-derived β-glucosidase; the cDNA sequence, the genomic DNA sequence, the amino acid sequence, and the amino acid sequence of the mature protein are shown in SEQ ID NO: 5, SEQ ID NO: 6, SEQ ID NO: 7, and SEQ ID NO: 8, respectively.

1. Method for Preparing a Steviol Glycoside and/or Steviol

The present invention provides a method for preparing steviol or a steviol glycoside having no monoglucoside bond and/or monoglucosyl ester bond comprising reacting a protein selected from the group consisting of proteins (a) to (c) shown below (hereinafter referred to as "the protein of the present invention") with a steviol glycoside having at least one monoglucoside bond and/or monoglucosyl ester bond, thereby cleaving said monoglucoside bond and/or monoglucosyl ester bond.

(a) a protein consisting of the amino acid sequence of SEQ ID NO: 3 or 4;

(b) a protein consisting of an amino acid sequence wherein 1 to 77 amino acids have been deleted, substituted, inserted, and/or added in the amino acid sequence of SEQ ID NO: 3 or 4, and having an activity to cleave a monoglucoside bond and/or monoglucosyl ester bond of a steviol glycoside; and (c) a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside.

While the protein shown in (b) or (c) above is typically a variant of a protein consisting of the amino acid sequence of SEQ ID NO: 3 or 4, these proteins also include proteins that can be artificially obtained using site-directed mutagenesis as described in, for example, "Sambrook & Russell, Molecular Cloning: A Laboratory Manual Vol. 4, Cold Spring Harbor Laboratory Press 2012", "Ausubel, Current Protocols in Molecular Biology, John Wiley & Sons 1987-1997", "Nuc. Acids. Res., 10, 6487 (1982)", "Proc. Natl. Acad. Sci. USA, 79, 6409 (1982)", "Gene, 34, 315 (1985)", "Nuc. Acids. Res., 13, 4431 (1985)", and "Proc. Natl. Acad. Sci. USA, 82, 488 (1985)".

Examples of the "protein consisting of an amino acid sequence wherein 1 to 77 amino acids have been deleted, substituted, inserted, and/or added in the amino acid sequence of SEQ ID NO: 3 or 4, and having an activity to cleave a monoglucoside bond and/or monoglucosyl ester bond of a steviol glycoside" include a protein consisting of an amino acid sequence wherein, for example, 1 to 77, 1 to 75, 1 to 70, 1 to 65, 1 to 60, 1 to 55, 1 to 50, 1 to 49, 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (one to several), 1 to 8, 1 to 7, 1 to 6, 1 to 5, 1 to 4, 1 to 3, 1 or 2, or 1 amino acid residue has been deleted, substituted, inserted, and/or added in the amino acid sequence of SEQ ID NO: 3 or 4, and having an activity to cleave a monoglucoside bond and/or monoglucosyl ester bond of a steviol glycoside. In general, the number of deleted, substituted, inserted, and/or added amino acid residues is preferably smaller.

Examples of such proteins include a protein having an amino acid sequence sharing 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more sequence identity with the amino acid sequence of SEQ ID NO: 3 or 4, and having an activity to cleave a monoglucoside bond and/or monoglucosyl ester bond of a steviol glycoside. In general, the value of sequence identity is preferably greater.

As used herein, the phrase "activity to cleave a monoglucoside bond and/or monoglucosyl ester bond of a steviol glycoside" refers to the activity to cleave (hydrolyze) either a monoglucoside or monoglucosyl ester or both (a monoglucoside and monoglucosyl ester) of a steviol glycoside, which is a glycoside wherein glucose is linked to the aglycone, steviol. In an embodiment, the bond to be cleaved is, but not limited to, a monoglucoside bond at the 13 position. In another embodiment, the bond to be cleaved is, but not limited to, a monoglucosyl ester bond at the 19 position.

The activity to cleave a monoglucoside bond or monoglucosyl ester bond of a steviol glycoside can be confirmed by reacting the protein of the present invention with a steviol glycoside having at least one monoglucoside bond and/or monoglucosyl ester bond, such as rebaudioside A, stevioside, or rubusoside, purifying the resulting reaction product, and analyzing the purified product using a known technique such as liquid chromatography (LC). The activity to hydrolyze a β-glucoside bond can be detected by using a medium containing X-β-Glc to culture a transformant genetically modified to express the protein of the present invention and confirming whether the cells and surrounding regions are stained blue. When X-β-Glc is hydrolyzed in the medium, the cells and surrounding regions are stained blue; thus, having blue color is considered to indicate the presence of the activity to hydrolyze a β-glucoside bond.

Alternatively, the activity to hydrolyze a β-glucoside bond can be examined by using p-nitrophenyl β-D-glucopyranoside as a substrate to measure the amount of p-nitrophenol produced by hydrolysis in terms of absorbance (A405).

The activity to hydrolyze a β-glucoside bond can be detected by using a medium containing X-β-Glc to culture a transformant genetically modified to express the protein of the present invention and confirming whether the cells and surrounding regions are stained blue.

The phrase "an amino acid sequence wherein 1 to 77 amino acid residues have been deleted, substituted, inserted, and/or added in the amino acid sequence of SEQ ID NO: 3 or 4" means that 1 to 77 amino acid residues have been deleted, substituted, inserted, and/or added at any 1 to 77 positions in the same sequence, wherein two or more of deletion, substitution, insertion, and addition may occur simultaneously.

Examples of amino acid residues that are interchangeable are shown below. The amino acid residues included in the same group are interchangeable.

Group A: leucine, isoleucine, norleucine, valine, norvaline, alanine, 2-aminobutanoic acid, methionine, o-methylserine, t-butylglycine, t-butylalanine, and cyclohexylalanine;

Group B: aspartic acid, glutamic acid, isoaspartic acid, isoglutamic acid, 2-aminoadipic acid, and 2-aminosuberic acid;

Group C: asparagine and glutamine;

Group D: lysine, arginine, ornithine, 2,4-diaminobutanoic acid, and 2,3-diaminopropionic acid;

Group E: proline, 3-hydroxyproline, and 4-hydroxyproline;

Group F: serine, threonine, and homoserine; and

Group G: phenylalanine and tyrosine.

The protein of the present invention in some embodiments does not contain a secretory signal peptide, because the secretory signal peptide is cleaved. Some other proteins of the present invention may further contain a secretory signal peptide, because the secretory signal peptide remains uncleaved. When the protein of the present invention contains a secretory signal peptide, it preferably contains the secretory signal peptide at its N-terminus. The secretory signal peptide refers to a peptide domain that serves to cause extracellular secretion of a protein bound to the secretory signal peptide. Amino acid sequences of such secretory signal peptides and polynucleotide sequences encoding such amino acid sequences have been well known and reported in the art.

The protein of the present invention can be obtained by, for example, expressing a polynucleotide encoding this protein (see "the polynucleotide of the present invention" described below) in appropriate host cells, although it can also be produced by a chemical synthesis method such as the Fmoc method (fluorenylmethyloxycarbonyl method) or the tBoc method (t-butyloxycarbonyl method). The protein of the present invention can also be chemically synthesized using a peptide synthesizer from AAPPTec LLC, Perkin Elmer Inc., Protein Technologies Inc., PerSeptive Biosystems, Applied Biosystems, or SHIMADZU CORPORATION, for example.

As used herein, the term "steviol glycoside" refers to a glycoside wherein glucose is linked to the aglycone, steviol. Examples of steviol and steviol glycosides are represented by the following formula (I).

[Formula 1]

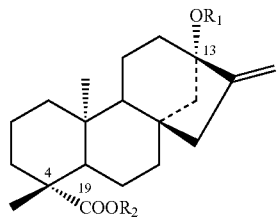

(I)

TABLE 1

| Compound Name | R₁ | R₂ |
|---|---|---|
| Rebaudioside D | Glc-β1,2-Glu (β1,3-Glu) | Glc-β1,2-Glu |
| Rebaudioside E | Glc-β1,2-Glu | Glc-β1,2-Glu |
| Rebaudioside A | Glc-β1,2-Glu (β1,3-Glu) | Glc- |
| Stevioside | Glc-β1,2-Glu | Glc- |
| Rubusoside | Glc- | Glc- |
| Steviol monoglucosyl ester | H | Glc- |
| Rebaudioside B | Glc-β1,2-Glu (β1,3-Glu) | H |
| Steviolbioside | Glc-β1,2-Glu | H |
| Steviolmonoside | Glc- | H |
| Steviol | H | H |

In the table shown above, "Glc" designates glucose and "Glc-" designates the inclusion of a monoglucoside bond ($R_1$ position) or monoglucosyl ester bond ($R_2$ position).

Among steviol glycosides, a steviol glycoside having at least one (for example, one or two) monoglucoside bond and/or monoglucosyl ester bond is, for example, a steviol glycoside selected from rebaudioside A, stevioside, rubusoside, steviolmonoside, and steviol monoglucosyl ester.

The method for preparing a steviol glycoside and/or steviol according to the present invention cleaves the monoglucoside bond and/or monoglucosyl ester bond, thereby producing a steviol glycoside and/or steviol having no monoglucoside bond and/or monoglucosyl ester bond (hereinafter referred to as "the steviol glycoside and/or steviol of the present invention" or collectively referred to as "the steviol glycoside of the present invention"). The steviol glycoside and/or steviol having no monoglucoside bond and/or monoglucosyl ester bond varies depending on the starting material, the "steviol glycoside having a monoglucoside bond and/or monoglucosyl ester bond", as follows. Examples thereof are shown below.

TABLE 2

| Starting Material | Steviol Glycoside of Present Invention |
|---|---|
| Rebaudioside A | Rebaudioside B |
| Stevioside | Steviolbioside |
| Rubusoside | Steviol |
| Steviolmonoside | |
| Steviol monoglucosyl ester | |

In the method for preparing a steviol glycoside and/or steviol according to the present invention, the steviol glycoside having at least one monoglucoside bond and/or monoglucosyl ester bond for use as the starting material can be obtained by extraction from *Stevia rebaudiana* or *Rubus suavissimus* followed by purification using known methods including extraction with an appropriate solvent (an aqueous solvent such as water, or an organic solvent such as an alcohol, ether, or acetone), a gradient between water and ethyl acetate or other organic solvent, high performance liquid chromatography (HPLC), gas chromatography, time-of-flight mass spectrometry (TOF-MS), and ultra (high) performance liquid chromatography (UPLC). Alternatively, a commercially-available product may be used as the steviol glycoside having at least one monoglucoside bond and/or monoglucosyl ester bond for use as the starting material. In some embodiments of the present invention, a monoglucoside bond and monoglucosyl ester bond of rubusoside are cleaved to produce steviol.

The method for preparing a steviol glycoside and/or steviol according to the present invention comprises reacting the protein of the present invention with a steviol glycoside having at least one monoglucoside bond and/or monoglucosyl ester bond, thereby cleaving said monoglucoside bond and/or monoglucosyl ester bond. The method of the present invention may further comprise purifying the steviol glycoside and/or steviol of the present invention which is produced in the above step and which has no monoglucoside bond and/or monoglucosyl ester bond.

The steviol glycoside according to the present invention which has no monoglucoside bond or glucosyl ester bond can be purified using known methods including extraction with an appropriate solvent (an aqueous solvent such as water, or an organic solvent such as an alcohol, ether, or acetone), a gradient between water and ethyl acetate or other organic solvent, high performance liquid chromatography (HPLC), gas chromatography, time-of-flight mass spectrometry (TOF-MS), and ultra (high) performance liquid chromatography (UPLC).

A different steviol glycoside can be produced by combining the protein of the present invention with another protein having a different activity.

Thus, in another embodiment, there is provided a method for producing at least one of rebaudioside B and steviol comprising reacting the protein of the present invention, a protein selected from the group consisting of proteins (d) to (f) shown below (hereinafter referred to as "the second active protein"), and a steviol glycoside having at least one monoglucoside bond and/or monoglucosyl ester bond:

(d) a protein consisting of the amino acid sequence of SEQ ID NO: 7 or 8;

(e) a protein consisting of an amino acid sequence wherein 1 to 77 amino acids have been deleted, substituted, inserted, and/or added in the amino acid sequence of SEQ ID NO: 7 or 8, and having an activity to cleave an unbranched β-1,2-glucoside bond of a steviol glycoside; and (f) a protein having an amino acid sequence having 90% or more sequence identity to the amino acid sequence of SEQ ID NO: 7 or 8, and having an activity to cleave an unbranched β-1,2-glucoside bond of a steviol glycoside.

In this method, the steviol glycoside having at least one monoglucoside bond and/or monoglucosyl ester bond may comprise one or more steviol glycosides selected from rebaudioside A, rebaudioside D, stevioside, rubusoside, steviolmonoside, and steviol monoglucosyl ester.

As used herein, the phrase "activity to cleave an unbranched β-1,2-glucoside bond of a steviol glycoside" refers to the activity to cleave an unbranched β-1,2-glucoside bond formed between two glucose residues in a steviol glycoside (a glycoside wherein glucose is linked to the aglycone, steviol). As used herein, the phrase "unbranched β-1,2-glucoside bond" refers to a β-1,2-glucoside bond wherein the β-1,2-glucoside-bonded glucose residues have no branched structure such as a β-1,3-glucoside bond ("Glc- β1,2-Glu" in Table 1 below). By contrast, when the β-1,2-glucoside-bonded glucose residues further have a branched structure such as a β-1,3-glucoside bond, the β-1,2-glucoside bond can be referred to as a branched β-1,2-glucoside bond ("Glc-β1,2-Glu (β1,3-Glu)" in Table 1 above).

The activity to cleave an unbranched β-1,2-glucoside bond of a steviol glycoside can be confirmed by reacting the protein of the present invention with a steviol glycoside having at least one β-1,2-glucoside bond, such as stevioside, purifying the resulting reaction product, and analyzing the purified product using a known technique such as liquid chromatography (LC).

The activity to hydrolyze a β-glucoside bond can be detected by using a medium containing X-β-Glc to culture a transformant genetically modified to express the protein of the present invention and confirming whether the cells and surrounding regions are stained blue. When X-β-Glc is hydrolyzed in the medium, the cells and surrounding regions are stained blue; thus, having blue color is considered to indicate the presence of the activity to hydrolyze a β-glucoside bond.

Alternatively, the activity to hydrolyze a β-glucoside bond can be examined by using p-nitrophenyl β-D-glucopyranoside as a substrate to measure the amount of p-nitrophenol produced by hydrolysis in terms of absorbance (A405).

The phrase "amino acid sequence wherein 1 to 77 amino acid residues have been deleted, substituted, inserted, and/or added in the amino acid sequence of SEQ ID NO: 7 or 8" means that 1 to 77 amino acid residues have been deleted, substituted, inserted, and/or added at any 1 to 77 positions in the same sequence, wherein two or more of deletion, substitution, insertion, and addition may occur simultaneously.

Examples of amino acid residues that are interchangeable are as previously described.

The second active protein may not contain any secretory signal peptide or may contain a secretory signal peptide. When the protein of the present invention contains a secretory signal peptide, it preferably contains the secretory signal peptide at its N-terminus. The secretory signal peptide refers to a peptide domain that serves to cause extracellular secretion of a protein bound to the secretory signal peptide. Amino acid sequences of such secretory signal peptides and polynucleotide sequences encoding such amino acid sequences have been well known and reported in the art.

The second active protein can be obtained by, for example, expressing a polynucleotide encoding this protein (such as a polynucleotide consisting of SEQ ID NO: 5 or 6) in appropriate host cells, although it can also be produced by a chemical synthesis method such as the Fmoc method (fluorenylmethyloxycarbonyl method) or the tBoc method (t-butyloxycarbonyl method). The second active protein can also be chemically synthesized using a peptide synthesizer from AAPPTec LLC, Perkin Elmer Inc., Protein Technologies Inc., PerSeptive Biosystems, Applied Biosystems, or SHIMADZU CORPORATION, for example.

The "steviol glycoside" is as previously described. The steviol glycoside having at least one unbranched β-1,2-glucoside bond is, for example, a steviol glycoside selected from rebaudioside D, rebaudioside E, stevioside, and steviolbioside.

The second active protein cleaves the unbranched β-1,2-glucoside bond. The resulting product varies depending on the starting material, the "steviol glycoside having at least one unbranched β-1,2-glucoside bond", as follows. Examples thereof are shown below.

TABLE 3

| Starting Material | Product |
| --- | --- |
| Rebaudioside D | Rebaudioside A |
| Rebaudioside E | Stevioside and Rubusoside |
| Stevioside | Rubusoside |
| Steviolbioside | Steviolmonoside |

In some embodiments, an unbranched β-1,2-glucoside bond of a steviol glycoside selected from stevioside, rebaudioside D, and steviolbioside is cleaved to produce a steviol glycoside selected from rubusoside, rebaudioside A, and steviolmonoside.

With the method for producing at least one of rebaudioside B and steviol comprising reacting the protein of the present invention, the second active protein, and one or more steviol glycosides selected from rebaudioside A, rebaudioside D, stevioside, rubusoside, steviolmonoside, and steviol monoglucosyl ester, based on the activity of the second active protein, rebaudioside B and steviol can be obtained as products from rebaudioside A, rebaudioside D, and stevioside as shown below.

TABLE 4

| Starting Material | Product |
| --- | --- |
| Rebaudioside D | Rebaudioside B |
| Rebaudioside A | |
| Stevioside | Steviol |
| Rubusoside | |
| Steviolmonoside | |
| Steviol monoglucosyl ester | |

2. Method for Producing the Steviol Glycoside and/or Steviol of the Present Invention Using a Non-Human Transformant The protein of the present invention is a koji mold-derived secretory enzyme or a variant thereof, and is expected to have high activity in an extracellular environment. In this case, the steviol glycoside of the present invention can be produced by introducing a polynucleotide encoding the protein of the present invention (see "the polynucleotide of the present invention" described below) into host cells derived from bacteria, fungi, plants, insects, non-human mammals, or the like, for extracellular expression of the protein of the present invention, and by reacting the protein of the present invention with a steviol glycoside having a monoglucoside bond and/or monoglucosyl ester bond. Alternatively, depending on the host, the steviol glycoside and/or steviol of the present invention can be produced by expressing the protein of the present invention in the host cells.

Thus, the present invention provides a method for producing a steviol glycoside and/or steviol having no monoglucoside bond and/or monoglucosyl ester bond comprising culturing a non-human transformant (hereinafter referred to as "the transformant of the present invention") obtained by introducing a polynucleotide selected from the group consisting of polynucleotides (a) to (e) shown below (hereinafter referred to as "the polynucleotide of the present invention") into a host producing a steviol glycoside having at least one monoglucoside bond and/or monoglucosyl ester bond:

(a) a polynucleotide consisting of the nucleotide sequence of SEQ ID NO: 1;

(b) a polynucleotide encoding a protein consisting of the amino acid sequence of SEQ ID NO: 3 or 4;

(c) a polynucleotide encoding a protein consisting of an amino acid sequence wherein 1 to 77 amino acids have been deleted, substituted, inserted, and/or added in the amino acid sequence of SEQ ID NO: 3 or 4, and having an activity to cleave a monoglucoside bond and/or monoglucosyl ester bond of a steviol glycoside;

(d) a polynucleotide encoding a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside; and (e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to cleave a monoglucoside bond and/or monoglucosyl ester bond of a steviol glycoside.

As used herein, the term "polynucleotide" refers to DNA or RNA.

Examples of the polynucleotide encoding the protein consisting of the amino acid sequence of SEQ ID NO: 3 or 4 include a polynucleotide consisting of the nucleotide sequence of SEQ ID NO: 1. Examples of the polynucleotide encoding the protein consisting of the amino acid sequence of SEQ ID NO: 8 include a polynucleotide consisting of the nucleotide sequence of SEQ ID NO: 5.

Examples of the "protein consisting of an amino acid sequence wherein 1 to 77 amino acids have been deleted, substituted, inserted, and/or added in the amino acid sequence of SEQ ID NO: 3 or 4, and having an activity to cleave a monoglucoside bond and/or monoglucosyl ester bond of a steviol glycoside" are as described above.

Examples of the "protein having an amino acid sequence having 90% or more sequence identity to the amino acid sequence of SEQ ID NO: 3 or 4, and having an activity to cleave a monoglucoside bond and/or monoglucosyl ester bond of a steviol glycoside" are as described above.

As used herein, the phrase "a polynucleotide which hybridizes under highly stringent conditions" refers to a polynucleotide obtained by means of a hybridization method such as colony hybridization, plaque hybridization, or Southern hybridization, using, as a probe, all of or a portion of a polynucleotide consisting of a nucleotide sequence complementary to the nucleotide sequence of SEQ ID NO: 1 or a polynucleotide consisting of a nucleotide sequence complementary to a nucleotide sequence encoding the amino acid sequence of SEQ ID NO: 3 or 4. For hybridization, methods as described in "Sambrook & Russell, Molecular Cloning: A Laboratory Manual Vol. 4, Cold Spring Harbor, Laboratory Press 2012" and "Ausubel, Current Protocols in Molecular Biology, John Wiley & Sons 1987-1997", for example, can be used.

As used herein, the term "highly stringent conditions" refers to, for example, the following conditions: 5×SSC, 5×Denhardt's solution, 0.5% SDS, 50% formamide, 50° C.; 0.2×SSC, 0.1% SDS, 60° C.; 0.2×SSC, 0.1% SDS, 62° C.; or 0.2×SSC, 0.1% SDS, 65° C.; although not limited thereto. Under these conditions, it is expected that DNA having a higher sequence identity will be efficiently obtained at a higher temperature. Note, however, that a plurality of factors such as temperature, probe concentration, probe length, ionic strength, time, and salt concentration are considered to affect the stringency of hybridization, and a person skilled in the art will be able to achieve the same stringency by selecting these factors as appropriate.

When a commercially available kit is used for hybridization, the Alkphos Direct Labelling and Detection System (GE Healthcare), for example, can be used. In this case, hybridization is accomplished in accordance with the protocol attached to the kit, i.e., a membrane may be incubated overnight with a labeled probe and then washed with a primary washing buffer containing 0.1% (w/v) SDS at 55 to 60° C. to detect the hybridized DNA. Alternatively, when a commercially available reagent (e.g., PCR labeling mix (Roche Diagnostics)) is used for digoxigenin (DIG) labeling of a probe during probe preparation based on all of or a portion of a nucleotide sequence complementary to the nucleotide sequence of SEQ ID NO: 1 of a nucleotide sequence complementary to a nucleotide sequence encoding the amino acid sequence of SEQ ID NO: 3 or 4, the DIG nucleic acid detection kit (Roche Diagnostics) may be used for detection of hybridization.

In addition to those described above, examples of other hybridizable polynucleotides include DNA sharing 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more sequence identity with DNA of the nucleotide sequence of SEQ ID NO: 1 or DNA encoding the amino acid sequence of SEQ ID NO: 3 or 4, as calculated by the homology search software BLAST using default parameters.

Note that the sequence identity of amino acid sequences or nucleotide sequences can be determined using the BLAST algorithm developed by Karlin and Altschul (Basic Local Alignment Search Tool) (Proc. Natl. Acad. Sci. USA 872264-2268, 1990; Proc Nati Acad Sci USA 90: 5873, 1993). When BLAST is used, default parameters in each program are used.

The polynucleotide of the present invention may further contain a pclynucleotide consisting of a nuclectide sequence encoding a secretory signal peptide. Preferably, the polynucleotide of the present invention contains, at its 5' end, the polynucleotide consisting of a nucleotide sequence encoding a secretory signal peptide. The secretory signal peptide is as described above. Such a secretory signal peptide can be selected as appropriate, depending on the host into which the polynucleotide of the present invention is to be introduced. For example, when the host is yeast, examples of secretory signal peptides include yeast-derived secretory signal peptides, such as MF(ALPHA)1 signal peptide, PHO5 signal peptide, and SUC2 signal peptide. Examples of polynucleotides encoding MF(ALPHA)1 signal peptide, PHO5 signal peptide, and SUC2 signal peptide include polynucleotides consisting of the nucleotide sequences shown in SEQ ID NO: 31, SEQ ID NO: 33, and SEQ ID NO: 35, respectively. The amino acid sequences of MF(ALPHA)1 signal peptide, PHO5 signal peptide, and SUC2 signal peptide are shown in SEQ ID NO: 32, SEQ ID NO: 34, and SEQ ID NO: 36, respectively. When the host is koji mold, examples of secretory signal peptides include koji mold-derived signal peptides, such as a peptide consisting of the amino acid sequence of SEQ ID NO: 28 or SEQ ID NO: 30. The polynucleotide encoding the peptide consisting of the amino acid sequence of SEQ ID NO: 28 or SEQ ID NO: 30 is a polynucleotide consisting of the nucleotide sequence of SEQ ID NO: 27 or SEQ ID NO: 29, respectively, for example.

The above-described polynucleotide of the present invention can be obtained using a known genetic engineering technique or a known synthesis technique.

The polynucleotide of the present invention is preferably inserted into an appropriate expression vector for introduction into a host.

An appropriate expression vector is typically configured to include:

(i) a promoter transcribable in host cells;
(ii) the polynucleotide of the present invention ligated to the promoter; and
(iii) an expression cassette containing, as constituent elements, signals that function in the host cells for transcription termination and polyadenylation of an RNA molecule.

Examples of methods for preparing such an expression vector include, although not particularly limited to, using plasmids, phages, cosmids, or the like.

The specific type of the vector is not particularly limited, and any vector expressible in host cells may be selected as appropriate. Specifically, an appropriate promoter sequence may be selected in accordance with the type of the host cells to ensure the expression of the polynucleotide of the present invention, and this promoter sequence and the polynucleotide of the present invention may then be integrated into any of various plasmids, for example, for use as an expression vector.

The expression vector of the present invention contains an expression control region (e.g., a promoter, a terminator, and/or a replication origin), depending on the type of the host into which the expression vector is to be introduced. For bacterial expression vectors, commonly used promoters (e.g., trc promoter, tac promoter, and lac promoter) are used. Examples of yeast promoters include glyceraldehyde-3-phosphate dehydrogenase promoter and PH05 promoter. Examples of filamentous fungi promoters include amylase and trpC. Moreover, examples of promoters for expression of a target gene in plant cells include cauliflower mosaic virus 35S RNA promoter, rd29A gene promoter, rbcS promoter, and mac-1 promoter configured to have the enhancer sequence of the above-mentioned cauliflower mosaic virus 35S RNA promoter at the 5'-side of *Agrobacterium*-derived mannopine synthase promoter sequence. Examples of promoters for animal cell hosts include viral promoters (e.g., SV40 early promoter and SV40 late promoter). Examples of promoters inducibly activated by external stimulation include mouse mammary tumor virus (MMTV) promoter, tetracycline-responsive promoter, metallothionein promoter, and heat-shock protein promoter.

The expression vector preferably contains at least one selection marker. For use as such a marker, auxotrophic markers (ura5, niaD), drug resistance markers (hygromycin, zeocin), geneticin resistance gene (G418r), copper resistance gene (CUP1) (Marin et al., Proc. Natl. Acad. Sci. USA, vol. 81, p. 337, 1984), cerulenin resistance genes (fas2m, PDR4) (Junji Inokoshi et al., Biochemistry, vol. 64, p. 660, 1992; Hussain et al., Gene, vol. 101, p. 149, 1991), and the like are available.

While the method for preparing (producing) the transformant of the present invention is not particularly limited, the transformant of the present invention may be prepared by, for example, introducing an expression vector containing the polynucleotide of the present invention into a host to transform the host. The host to be used herein is not particularly limited as long as it produces a steviol glycoside having at least one monoglucoside bond and/or monoglucosyl ester bond, and may include not only a plant such as *Stevia rebaudiana* that produces a steviol glycoside having at least one monoglucoside bond and/or monoglucosyl ester bond, but also a host obtained by introducing a gene required for the production of a steviol glycoside having at least one monoglucoside bond and/or monoglucosyl ester bond into cells or an organism that does not originally produce a steviol glycoside having at least one monoglucoside bond and/or monoglucosyl ester bond. Examples of the "gene required for the production of a steviol glycoside having at least one monoglucoside bond and/or monoglucosyl ester bond" include genes having steviol or steviol glycoside synthesis activity such as those described in WO 2011093509. Any of conventionally known various types of cells or organisms can be suitably used as the cells or organism to be transformed. Examples of the cells to be transformed include bacteria such as *Escherichia coli*, yeast (budding yeast *Saccharomyces cerevisiae*, fission yeast *Schizosaccharomyces pombe*), filamentous fungi (koji mold *Aspergillus oryzae, Aspergillus sojae*), plant cells, and non-human animal cells. Appropriate media and conditions for culturing the above-described host cells are well known in the art. Likewise, the organism to be transformed is not particularly limited, and examples include various microorganisms, plants, and non-human animals described above as examples of host cells. The transformant is preferably yeast or a plant.

For transformation of the host cells, commonly used known methods can be used. For example, transformation can be accomplished using electroporation (Mackenxie, D. A. et al., Appl. Environ. Microbiol., vol. 66, p. 4655-4661, 2000), the particle delivery method (described in JP 2005-287403 A entitled "Breeding Method of Lipid Producing Fungi"), the spheroplast method (Proc. Natl. Acad. Sci. USA, vol. 75, p. 1929, 1978), the lithium acetate method (J. Bacteriology, vol. 153, p. 163, 1983), and other methods as described in Methods in yeast genetics, 2000 Edition: A Cold Spring Harbor Laboratory Course Manual, although not limited thereto. When a gene is introduced into a plant or into tissues or cells derived from a plant, a method selected from the *Agrobacterium* method (Plant Molecular Biology Manual, Gelvin, S. B. et al., Academic Press Publishers), particle gun method, PEG method, electroporation, etc. can be used as appropriate.

For other standard molecular biological techniques, reference may be made to "Sambrook & Russell, Molecular Cloning: A Laboratory Manual Vol. 4, Cold Spring Harbor Laboratory Press 2012" and "Methods in Yeast Genetics, A laboratory manual (Cold Spring Harbor Laboratory Press, Cold Spring Harbor, N.Y.)", for example.

When the transformant is yeast or koji mold, the transformant is obtained by introducing a recombinant vector containing the polynucleotide of the present invention into yeast or koji mold such that a polypeptide encoded by the polynucleotide can be expressed. The yeast or koji mold transformed with the polynucleotide of the present invention expresses a higher level of the protein of the present invention than in the wild-type counterpart. Thus, the expressed protein of the present invention reacts with the steviol glycoside having at least one monoglucoside bond and/or monoglucosyl ester bond produced in the yeast or koji mold, thereby cleaving said monoglucoside bond and/or monoglucosyl ester bond.

As a result, the steviol glycoside of the present invention having no monoglucoside bond and/or monoglucosyl ester bond is produced in the cells or culture medium of the yeast or koji mold, preferably in the culture medium.

When the transformant is a plant, the transformant is obtained by introducing a recombinant vector containing the polynucleotide of the present invention into a plant such that a protein encoded by the polynucleotide can be expressed. The plant to be transformed in the present invention refers to any of whole plants, plant organs (e.g., leaves, petals, stems, roots, and seeds), plant tissues (e.g., epidermis, phloem, parenchyma, xylem, vascular bundles, palisade tissue, and spongy parenchyma) or plant cultured cells, or various forms of plant cells (e.g., suspension cultured cells), protoplasts, leaf sections, calli, and the like. The plant used for transformation is not particularly limited as long as it is a plant that produces a steviol glycoside having at least one monoglucoside bond and/or monoglucosyl ester bond, or a plant that does not originally produce a steviol glycoside having at least one monoglucoside bond and/or monoglucosyl ester bond, but can produce a steviol glycoside having at least monoglucoside bond and/or monoglucosyl ester bond through the introduction of a required gene. The plant used for transformation may be a plant in the class of either monocotyledons or dicotyledons. The introduction of the polynucleotide of the present invention into the plant can be confirmed by using PCR, Southern hybridization, or Northern hybridization, for example. Once a transformed plant in which the polynucleotide of the present invention has been integrated into the genome is obtained, progeny plants can be produced by sexual or asexual reproduction of the plant. Moreover, seeds, fruits, cuttings, tubers, root tubers, rootstocks, calli, protoplasts or the like can be obtained from this plant or progeny plants thereof, or clones thereof, and used to achieve mass production of the plant. The plant transformed with the polynucleotide of the present invention (hereinafter, "the plant of the present invention") contains a greater amount of the protein of the present invention than in the wild-type counterpart. Thus, the protein of the present invention reacts with the steviol glycoside having at least one monoglucoside bond and/or monoglucosyl ester bond produced in the plant of the present invention, thereby cleaving said monoglucoside bond and/or monoglucosyl ester bond. As a result, the steviol glycoside of the present invention having no monoglucoside bond and/or monoglucosyl ester bond is produced in the plant.

The transformant in some embodiments of the present invention or the culture medium thereof has a content of the Steviol glycoside of the present invention higher than that in the wild-type counterpart, and an extract or the culture medium of the transformant contains a high concentration of the Steviol glycoside of the present invention. An extract of the transformant of the present invention can be obtained by homogenating the transformant with glass beads, a homogenizer, or a sonicator, for example, centrifuging the homogenate, and collecting the supernatant. When the Steviol glycoside of the present invention accumulates in the culture medium, the transformant and the culture supernatant may be separated using a standard method (e.g., centrifugation or filtration) after the completion of culture, thereby obtaining the culture supernatant containing the Steviol glycoside of the present invention.

The extract or culture supernatant thus obtained may be further subjected to a purification step. The Steviol glycoside of the present invention may be purified in accordance with a standard separation and purification method. Specific methods for purification are the same as described above.

3. Method for Preparing the Steviol Glycoside and/or Steviol of the Present Invention Using an Enzyme Agent Derived from Non-Human Transformed Cells The steviol glycoside of the present invention can be produced by using an enzyme agent derived from transformed cells expressing the protein of the present invention, which are obtained by introducing the polynucleotide of the present invention into host cells derived from bacteria, fungi, plants, insects, non-human mammals, or the like, for expression of the protein of the present invention, i.e., by contacting the enzyme agent derived from transformed cells expressing the protein of the present invention with a steviol glycoside having at least one monoglucoside bond and/or monoglucosyl ester bond. The "enzyme agent derived from transformed cells" is not limited as long as it is prepared using transformed cells, and contains the protein of the present invention. Examples of the enzyme agent include transformed cells themselves, a transformed cell homogenate itself, transformed cell culture supernatant itself, and a purified product thereof. Thus, the present invention provides a method for preparing a steviol glycoside and/or steviol having no monoglucosyl ester bond comprising contacting an enzyme agent derived from a non-human transformed cell obtained by introducing, into a host cell, a polynucleotide selected from the group consisting of polynucleotides (a) to (e) shown below, with a steviol glycoside having at least one monoglucoside bond and/or monoglucosyl ester bond, thereby cleaving said monoglucoside bond and/or monoglucosyl ester bond:

(a) a polynucleotide consisting of the nucleotide sequence of SEQ ID NO: 1;

(b) a polynucleotide encoding a protein consisting of the amino acid sequence of SEQ ID NO: 3 or 4;

(c) a polynucleotide encoding a protein consisting of an amino acid sequence wherein 1 to 77 amino acids have been deleted, substituted, inserted, and/or added in the amino acid sequence of SEQ ID NO: 3 or 4, and having an activity to cleave a monoglucoside bond and/or monoglucosyl ester bond of a steviol glycoside;

(d) a polynucleotide encoding a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside; and (e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to cleave a monoglucoside bond and/or monoglucosyl ester bond of a steviol glycoside.

The polynucleotide selected from the group consisting of polynucleotides (a) to (e) shown above is the polynucleotide of the present invention, which is the same as described above.

The polynucleotide of the present invention may further contain a polynucleotide consisting of a nucleotide sequence encoding a secretory signal peptide. Preferably, the polynucleotide of the present invention contains, at its 5' end, the polynucleotide consisting of a nucleotide sequence encoding a secretory signal peptide. The secretory signal peptide and the polynucleotide consisting of a nucleotide sequence encoding the secretory signal peptide are the same as described above.

The polynucleotide of the present invention is preferably inserted into an appropriate expression vector for introduction into host cells. An appropriate expression vector is the same as described above.

While the method for preparing the transformed cells of the present invention is not particularly limited, the transformed cells of the present invention may be prepared by, for example, introducing an expression vector containing the polynucleotide of the present invention into host cells to transform the host cells. The cells to be transformed are the same as described above. The method for transforming the host cells is as described above.

The transformed cells of the present invention are obtained by, for example, introducing a recombinant vector containing the polynucleotide of the present invention into the host cells such that a polypeptide encoded by the polynucleotide can be expressed. The host cells transformed with the polynucleotide of the present invention express a higher level of the protein of the present invention than in the wild-type counterpart. Thus, the steviol glycoside and/or steviol of the present invention can be obtained by using an enzyme agent derived from transformed cells expressing the protein of the present invention, i.e., by contacting the enzyme agent derived from transformed cells expressing the protein of the present invention with a steviol glycoside having at least one monoglucoside bond and/or monoglucosyl ester bond.

The term "contact" refers to causing the enzyme agent derived from the transformed cells of the present invention and the steviol glycoside having at least one monoglucoside bond and/or monoglucosyl ester bond to exist in the same reaction or culture system. The term "contact" includes, for example, adding the steviol glycoside having at least one monoglucoside bond and/or monoglucosyl ester bond to a container containing the enzyme agent derived from the transformed cells of the present invention, mixing the enzyme agent derived from the transformed cells of the present invention and the steviol glycoside having at least one monoglucoside bond and/or monoglucosyl ester bond, and adding the enzyme agent derived from the transformed cells of the present invention to a container containing the steviol glycoside having at least one monoglucoside bond and/or monoglucosyl ester bond.

The terms "steviol glycoside", "steviol glycoside having at least one monoglucoside bond and/or monoglucosyl ester bond", "steviol glycoside and/or steviol having no monoglucosyl ester bond", "monoglucoside bond and/or monoglucosyl ester bond", and "activity to cleave a monoglucoside bond and/or monoglucosyl ester bond of a steviol glycoside" are the same as described above.

The Steviol glycoside of the present invention thus obtained can be used for such purposes as the production of foods, sweeteners, flavors, pharmaceutical products, and industrial raw materials (raw materials for cosmetics, soaps, and the like), for example, in accordance with conventional methods.

Examples of foods include nutritional supplements, health foods, functional foods, foods for children, and foods for the elderly. As used herein, the term "foods" refers collectively to edible materials in the form of solids, fluids, liquids, and mixtures thereof.

Note that all documents, as well as laid-open application publications, patent application publications, and other patent documents cited herein shall be incorporated herein by reference.

EXAMPLES

The present invention will be more specifically described hereinafter with reference to examples, which are not intended to limit the scope of the present invention.

1. Cloning of Steviol-Hydrolyzing Enzyme Genes 1-(1) Genes

AO090009000356 and AO090701000274 were cloned and expressed in yeast to examine the activity.

1-(2) Cloning of cDNAs of Koji Mold

Koji mold *Aspergillus oryzae* var. *Brunneus* (IFO30102) was inoculated to a GY plate (2% glucose, 0.5% yeast extract, and 2% agar), and cultured at 25° C. for 3 days. The grown cells were collected from the GY plate, and total RNA was extracted using RNeasy (QIAGEN). A cDNA was synthesized using the SuperScript Double-Stranded cDNA Synthesis Kit (Life Technologies).

The following primers were designed based on the DNA sequence of AO090009000356 and AO090701000274:

```
AO090009000356 (hereinafter expressed as AOBGL1)
AOBGL1-1:
                                       (SEQ ID NO: 9)
5'-AGATCTATGAAGCTTGGTTGGATCGAGGT-3'

AOBGL1-2
                                       (SEQ ID NO: 10)
5'-GTCGACTTACTGGGCCTTAGGCAGCGA-3'

AO090701000274 (hereinafter expressed as AOBGL3)
AOBGL3-1:
                                       (SEQ ID NO: 11)
5;-GCGGCCGCatggtttccggtgtctttacgaagg-3'

AOBGL3-2:
                                       (SEQ ID NO: 12)
5'-GGATCCtcactgcacatagaaagtagcattgcc-3'.
```

Approximately 2.6 kbp or 2.3 kbp of a DNA fragment amplified by PCR using ExTaq (Takara Bio), using each of the cDNAs synthesized as described above as a template, was cloned using the TOPO-TA cloning Kit (Life Technologies). Each of the plasmids obtained herein was designated as pCR-AOBGL1 or pCR-AOBGL3.

2. Expression in Yeast 2-(i) Construction of Yeast Expression Vectors and Acquisition of Transformed Strains A DNA fragment obtained by digesting the yeast expression vector pYE22m (Biosci. Biotech. Biochem., 59, 1221-1228, 1995) with restriction enzymes BamHI and SalI and approximately 2.6 kbp of a DNA fragment obtained by digesting pCR-AOBGL1 with restriction enzymes BglII and SalI were ligated using the DNA Ligation Kit Ver.1 (Takara Bio), and the resulting plasmid was designated as pYE-AOBGL1. Additionally, a DNA fragment obtained by digesting pYE22 mN with restriction enzymes NotI and BamHI and approximately 2.3 kbp of a DNA fragment obtained by digesting pCR-AOBGL3 with restriction enzymes NotI and BamHI were ligated in the same manner as above, and the resulting plasmid was designated as pYE-AOBGL3. *S. cerevisiae* strain EH13-15 (trp1, MATα) (Appl. Microbiol. Biotechnol., 30, 515-520, 1989) was used as the parental strain for transformation.

Each of the plasmids pYE22m (control), pYE-AOBGL1 (for expression of AOBGL1), and pYE-AOBGL3 (for expression of AOB3GL3) was used to transform strain EH13-15 in accordance with the lithium acetate method. A strain that grew on SC-Trp (containing, per liter, 6.7 g of Yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 0.6 g of uracil) agar medium (2% agar) was selected as the transformed strain.

The selected strain was applied to SC-Trp agar medium containing 0.004% of X-β-Glc, and cultured at 30° C. for 3 days. As a result, neither the strain transformed with any of the plasmids pYE-AOBGL1 and pYE-AOBGL3 nor the strain transformed with the control pYE22m was stained blue, and no X-β-Glc degrading activity was confirmed.

Meanwhile, one platinum loop of the selected strain was inoculated to 10 mL of SC-Trp liquid medium supplemented with 1/10 volume of 1M potassium phosphate buffer, and cultured with shaking at 30° C. and 125 rpm for 2 days. The resulting culture was separated into the culture supernatant and cells by centrifugation. The cells were suspended in 50 mM sodium phosphate buffer (pH 7.0) containing 0.1% CHAPS solution and then homogenated with glass beads, and the supernatant obtained by centrifugation was used as the cell homogenate. The obtained culture supernatant or cell homogenate was examined for its pNP-β-Glc activity.

As a result, both the culture supernatant and cell homogenate for each type of transformed strain including the control exhibited pNP-β-Glc degrading activity, and no significant difference in activity was observed between them.

These results suggested that the introduction of the plasmid pYE-AOBGL1 or pYE-AOBGL3 into yeast strain EH13-15 does not allow expression of an activated protein having β-glucosidase activity. Moreover, the need for the deletion of an endogenous gene responsible for β-glucosidase activity in yeast was indicated.

2-(2) Creation of Δexg1 Δexg2 Yeast Host Strains

A strain with deletion of the EXG1 (YLR300w) gene considered to be responsible for most of the extracellular β-glucosidase activity in yeast and its homolog EXG2 (YDR261c) gene was used as the host strain for transformation. This host strain was created as follows:

Each of Δexg1 strain (MATalpha his3Δ1 leu2Δ0 lys2Δ0 ura3Δ0; clone ID: 15210; Open Bio Systems) and Δexg2 strain (MATa his3Δ1 leu2Δ0 met15Δ0 ura3Δ0; clone ID: 3620; Open BioSystems) was applied to YPD agar medium, and cultured at 30° C. for 2 days. The cells of each strain were scraped with a platinum loop and mixed on SC-Met, Lys (containing, per liter, 6.7 g of Yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 1.5 g of phenylalanine, 11.25 g of serine, 0.9 g of tyrosine, 4.5 g of valine, 6 g of threonine, 1.2 g of tryptophan, and 0.6 g of uracil) agar medium (2% agar), and the mixture was cultured at 30° C. for 2 days. The grown strain was considered to be a hetero-diploid obtained by hybridization of the two strains. The obtained strain was applied to YPD agar medium and cultured at 30° C. for 2 days, and then the cells were scraped with a platinum loop, applied to 0.5% potassium acetate agar medium (2% agar), and cultured at room temperature for 5 days, thus forming spores. Tetrad dissection was performed to separate haploid strains. Genotypes of the obtained strains were confirmed by PCR, and Δexg1 Δexg2-1 strain (his3Δ1 leu2Δ0 lys2Δ0 ura3Δ0) was selected.

Using the genomic DNA of yeast strain S288C, PCR was performed with the following primers TRP1-F and TRP1-R, using KOD-Plus (Toyobo). Approximately 2.7 kbp of the amplified DNA fragment was cloned using the Zero Blunt TOPO PCR cloning Kit (Life Technologies), thus obtaining a plasmid pCR-TRP1.

```
TRP1-F:
                                        (SEQ ID NO: 13)
TACTATTAGCTGAATTGCCACTGCTATCG

TRP1-R:
                                        (SEQ ID NO: 14)
TCTACAACCGCTAAATGTTTTTGTTCG
```

2.7 kbp of a DNA fragment obtained by digesting pPRGINFRT3-103 (Japanese Patent Laid-Open No. 2001-120276) with restriction enzymes EcoRI and HindIII was blunt-ended using the Blunting Kit (Takara Bio), and then ligated to a DNA fragment obtained by digesting the plasmid pCR-TRP1 with restriction enzymes HpaI and StuI, using Ligation High (Toyobo), thus obtaining a plasmid pCR-Δtrp1:URA3-FRT. Using this plasmid as a template, PCR was performed with the primers TRP1-F and TRP1-R, using KOD-Plus (Toyobo). Then, 4.4 kbp of the resulting DNA fragment was used to transform Δexg1 Δexg2-1 strain in accordance with the lithium acetate method, and a strain that grew on SC-Ura (containing, per liter, 6.7 g of Yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 1.2 g of tryptophan) agar medium (2% agar) was selected as the transformed strain. The transformed strain was cultured on YPGal medium (yeast extract: 2%, polypeptone: 1%, galactose: 2%) and then applied to SC+5-FOA (containing, per liter, 6.7 g of Yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, 1.2 g of tryptophan, and 0.6 g of uracil) agar medium (2% agar), and a grown strain was obtained as Δexg1 Δexg2-2 strain and used as the host for the following transformation.

2-(3) Substitution of Secretory Signal Sequences and Expression in Yeast

Nineteen amino acids (SEQ ID NO: 28) at the N-terminus of AOBGL1p and 22 amino acids (SEQ ID NO: 30) at the N-terminus of AOBGL3 are estimated to be secretory signal sequences.

Thus, for secretion and expression of each of AOBGL1 and AOBGL3 in yeast, the estimated secretory signal sequence was substituted with a secretory signal sequence of a yeast secretory protein. Initially, the following oligodeoxynucleotides were synthesized and annealed, and then inserted into the EcoRI site of the vector pYE22m, thus creating pYE-PacNhe.

```
PacI-NheI-F:
                                        (SEQ ID NO: 15)
5'-AATTAATTAAGAGCTAGCG-3'

PacI-NheI-R:
                                        (SEQ ID NO: 16)
5'-TTAATTCTCGATCGCTTAA-3'
```

Using the plasmid pCR-AOBGL1 or pCR-ASBGL1 as a template, PCR was performed with the following primers Bgl2-AOBGL1-F and AOBGL1-2, using KOD-Plus (Toyobo). Approximately 2.5 kbp of a DNA fragment obtained by digesting the PCR-amplified DNA fragment with restriction enzymes BglII and SalI was inserted into the sites of restriction enzymes BamHI and SalI of the vector pYE-PacNhe, thus constructing a plasmid pYE-PN-AOBGL1.

```
Bgl2-AOBGL1-F:
                                           (SEQ ID NO: 17)
5'-TAAGATCTAAGGATGATCTCGCGTACTCCCC-3'

AOBGL1-2:
                                           (SEQ ID NO: 10)
5'-GTCGACTTACTGGGCCTTAGGCAGCGA-3'
```

Using the plasmid pCR-ASBGL3 as a template, PCR was performed with the following primers Bam-ASBGL3-F and Sal-ASBGL3-R, using KOD-Plus (Toyobo). Approximately 2.3 kbp of a DNA fragment obtained by digesting the PCR-amplified DNA fragment with restriction enzymes BamHI and SalI was inserted into the sites of restriction enzymes BamHI and SalI of the vector pYE-PacNhe, thus constructing a plasmid pYE-PN-AOBGL3.

```
Bam-AOBGL3-F:
                                           (SEQ ID NO: 19)
5'-AAGGATCCCAAGATGAGAAGCCTCGCTACAAGG-3

Sal-AOBGL3-R:
                                           (SEQ ID NO: 20)
5'-GGGTCGACTCACTGCACATAGAAAGTAGCATTGCC-3'
```

The primers shown below were designed to construct a plasmid for expression of a protein in which the estimated secretory signal sequence of AOBGL1 or AOBGL3 was substituted with the secretory signal sequence MF(ALPHA)1 (YPL187W) (the sequence of positions 1 to 19 of the amino acid sequence (SEQ ID NO: 32) shown in FIG. 2A), PH05 (YBR093C) (the sequence of positions 1 to 17 of the amino acid sequence (SEQ ID NO: 34) shown in FIG. 2B), or SUC2 (YIL162W) (the sequence of positions 1 to 19 of the amino acid sequence (SEQ ID NO: 36) shown in FIG. 2C) of a yeast secretory protein.

```
ScPHO5-F:
                                           (SEQ ID NO: 21)
5'-TAAATGTTTAAATCTGTTGTTTATTCAATTTTAGCCGCTTCTTTGGC
CAATGCAG-3

ScPHO5-R:
                                           (SEQ ID NO: 22)
5'-CTAGCTGCATTGGCCAAAGAAGCGGCTAAAATTGAATAAACAACAGA
TTTAAACATTTAAT-3'

ScSUC2-F:
                                           (SEQ ID NO: 23)
5'-TAAATGCTTTTGCAAGCTTTCCTTTTCCTTTTGGCTGGTTTTGCAGC
CAAAATATCTGCAG-3'

ScSUC2-R:
                                           (SEQ ID NO: 24)
5'-TAAATGAGATTTCCTTCAATTTTTACTGCAGTTTTATTCGCAGCATC
CTCCGCATTAGCTG-3'

ScMF1-F:
                                           (SEQ ID NO: 25)
5'-TAAATGAGATTTCCTTCAATTTTTACTGCAGTTTTATTCGCAGCATC
CTCCGCATTAGCTG-3'

ScMF1-R:
                                           (SEQ ID NO: 26)
5'-CTAGCAGCTAATGCGGAGGATGCTGCGAATAAAACTGCAGTAAAAAT
TGAAGGAAATCTCATTTAAT-3'
```

The combination of ScPHO5-F and ScPHO5-R, the combination of ScSUC2-F and ScSUC2-R, and the combination of ScMF1-F and ScMF1-R were each annealed, and then ligated to the plasmid pYE-PN-AOBGL1 or pYE-PN-ASBGL1 digested with restriction enzymes PacI and NheI, thus obtaining the following plasmids:

pYE-PHC5s-AOBGL1 (for expression of PHO5s-AOBGL1)
pYE-SUC2s-AOBGL1 (for expression of SUC2s-AOBGL1)
pYE-MF1s-AOBGL1 (for expression of MF1s-AOBGL1)
pYE-PHO5s-AOBGL3 (for expression of PHO5s-AOBGL3)
pYE-SUC2s-AOBGL3 (for expression of SUC2s-AOBGL3)
pYE-MF1s-AOBGL3 (for expression of MF1s-AOBGL3)

Δexg1 Δexg2-2 strain was transformed with these plasmids in accordance with the lithium acetate method, and a strain that grew on SC-Trp agar medium was selected as the transformed strain.

The obtained transformed strain was applied to SD-Trp agar medium containing 0.004% of X-β-Glc, and cultured at 30° C. for 3 days. As a result, the cells and surrounding regions were stained blue in the strain transformed with pYE-PHO5s-AOBGL1, pYE-SUC2s-AOBGL1, pYE-MF1s-ACBGL1, pYE-PHO5s-ASBGL1, pYE-SUC2s-ASBGL1, or pYE-MF1s-ASBGL1, suggesting that these strains had X-βGlc hydrolyzing activity.

Meanwhile, in the strain transformed with the plasmid for expression of AOBGL3, the cells and surrounding regions were not stained blue, and the activity to hydrolyze X-β-Glc was not confirmed.

In the strain transfected with a control vector, the cells and surrounding regions were not stained blue, showing that the strain did not have the activity to hydrolyze X-β-Glc.

One platinum loop of the obtained transformed strain was inoculated to a liquid medium obtained by mixing 10 mL of SD-Trp liquid medium and 1 mL of 1M potassium phosphate buffer, and cultured with shaking at 30° C. for 2 days. The culture was separated into the cells and culture supernatant by centrifugation. 50 μL of the culture supernatant, 50 μL of a 0.2M sodium citrate buffer, 50 μL of a 20 mM aqueous pNP-βGlc solution, and 50 μL of water were mixed, and the mixture was reacted at 37° C. for 1 hour, after which the increase in absorbance at 405 nm due to β-glucosidase activity was examined. When AOBGL1 was expressed, the β-glucosidase activity was confirmed as shown in Table 5. AOBGL1 was considered to be expressed at the highest level when substituted with the MF1 signal sequence.

TABLE 5

| β-glucosidase activity in culture medium (Increase in absorbance at 405 nm; reaction for 1 hour) | |
|---|---|
| Plasmid | Δ 405 nm |
| pYE-MF1s-AOBGL1 | 0.508 |
| pYE-PHO5s-AOBGL1 | 0.37 |
| pYE-SUC2s-AOBGL1 | 0.369 |
| pYE22m | 0 |

However, when AOBGL3 was expressed, the β-glucosidase activity was not confirmed under the same conditions.

2-(4) Activity of Recombinant Enzyme on Steviol Glycoside

AOBGL1 was confirmed to have an activity to convert stevioside into rubusoside.

3. Expression of AOBGL3 in Koji Mold 3-(1) Construction of Koji Mold Expression Vector A DNA fragment obtained by digesting a koji mold vector pUNA (National Research Institute of Brewing) with a restriction enzyme SmaI, and approximately 2.3 kbp of a DNA fragment obtained by digesting the plasmid pCR-AOBGL3 with restriction enzymes NotI and BamHI and blunt-ending the end using Blunting Kit (Takara Bio), were ligated to obtain a plasmid pUNA-AOBGL3.

3-(2) Transformation of Koji Mold

Koji mold was transformed as follows.

*Aspergillus oryzae* niaD300 strain (National Research Institute of Brewing) was used as a host. The host strain was inoculated to a PDA plate and cultured at 30° C. for about 1 week. In order to obtain a conidial suspension, the resulting conidia were suspended by adding 0.1% tween 80 and 0.8% NaCl. The suspension was filtered through Miracloth and then centrifuged to collect the conidia. The conidia were then washed with 0.1% tween 80 and 0.8% NaCl and suspended in sterilized water.

The conidia were applied to a CD plate, and DNA was introduced into the conidia by the particle delivery method. This was performed using PDS-1000/He (Bio-Rad), tungsten M-10 particles, and a 1100 psi rupture disc at a distance of 3 cm. A strain that grew on a CD plate (containing, per liter, 6 g of $NaNO_3$, 0.52 g of KCl, 1.52 g of $KH_2PO_4$, 10 g of glucose, 2 ml of 1M $MgSO_4$, 1 ml of a trace element solution (containing, per liter, 1 g of $FeSO_4*7H_2O$, 8.8 g of $ZnSO_4.7H_2O$, 0.4 g of $CuSO_4.5H_2O$, 0.1 q of $NaB_4O_7.10H_2O$, and 0.05 g of $(NH_4)_6Mo_7O_{24}.4H_2O$), and 20 g of agar (pH 6.5)) was selected as the transformed strain.

3-(3) Preparation of Conidial Suspension

BGL3-1 stain or C-1 strain was inoculated to a CD plate and cultured at 30° C. for 7 days to form conidia. In order to obtain a conidial suspension, the conidia were suspended by adding 0.1% tween 80 and 0.8% NaCl. The suspension was filtered through Miracloth and then centrifuged to collect the conidia. The conidia were then washed with 0.1% tween 80 and 0.8% NaCl and suspended in sterilized water to prepare a conidial suspension.

3-(4) Production of AOBGL3 by Liquid Culture

Conidia of BGL3-1 strain or C-1 strain were inoculated to a liquid culture medium for enzyme production (containing, per liter, 100 g of maltose, 1 g of Bacto-tryptone, 5 g of yeast extract, 1 g of $NaNO_3$, 0.5 g of $K_2HPO_4$, 0.5 g of $MgSO_4.7H_2O$, and 0.01 g of $FeSO_4.7H_2O$) and cultured with shaking at 30° C. for 2 days. The medium was filtered through Miracloth to remove the cells and further filtered through a membrane filtration system (IWAKI) to collect the supernatant. The supernatant was then concentrated by ultra-filtration through Amicon Ultra-15 50k (Merck), and the buffer was replaced with a 50 mM sodium phosphate buffer (pH 7.0) containing 0.1% CHAPS to obtain a crude enzyme solution.

3-(5) Examination of Activity (Liquid Culture)

The activity on various substrates was examined. Both the pNP-β-Glc:BGL3-1 strain and C-1 strain were stained yellow, showing that both had the activity to hydrolyze pNP-β-Glc.

The X-β-Glc:BGL3-1 strain was stained blue, showing that it had the activity to hydrolyze X-β-Glc. By contrast, the C-1 strain was not stained blue, which was considered to indicate that the C-1 strain did not have the activity to hydrolyze X-β-Glc. The activity on X-β-Glc was attributed to an AOBGL3 gene product.

3-(6) Activity to Hydrolyze Steviol Glycoside

An enzyme solution derived from BGL3-1 strain or C-1 strain (liquid culture or plate culture) was examined for the activity to hydrolyze steviol glycosides (rubusoside) as follows.

Reaction Conditions

50 μg/ml of substrate, 20 μl of the enzyme solution, and a 50 mM sodium citrate buffer (pH 5.0) were mixed to a total volume of 100 μl, and the mixture was reacted at 50° C. The reaction mixture was passed through Sep-Pak C18 (Waters) washed with acetonitrile and equilibrated with water. The reaction product was subsequently washed with 20% acetonitrile and then eluted with 50% acetonitrile. The eluate was evaporated to dryness with SpeedVac. The resulting product was dissolved in 100 μL of 80% acetonitrile, and the solution was subjected to HPLC.

The conditions for HPLC were as follows:

Column: COSMOSIL $5C_{18}$-AR-II 4.6 mm I.D.×250 mm (Nacalai Tesque)

Mobile phase: A; acetonitrile, B;

B conc. 70%→30% 40 min linear gradient

Flow rate: 1 ml/min

Temperature: 40° C.

Detection: UV 210 nm

In summary, the enzyme activity to hydrolyze the glucoside bond at the 13 position of rubusoside and the glucosyl ester bond at the 19 position of rubusoside was exhibited through expression of AOBGL3. In view of the fact that an intermediate, steviol monoglucosyl ester, was detected in addition to steviol in the reaction with rubusoside, the AOBGL3 protein was found to be an enzyme which, although capable of hydrolyzing both the glucoside bond at the 13 position of rubusoside and the glucosyl ester bond at the 19 position of rubusoside, preferentially hydrolyzes the glucoside bond at the 13 position.

The invention claimed is:

1. A method for preparing a steviol glycoside and/or steviol comprising reacting a protein selected from the group consisting of proteins (a) to (c) shown below with a steviol glycoside having at least one monoglucoside bond and/or monoglucosyl ester bond, thereby cleaving said monoglucoside bond and/or monoglucosyl ester bond:

(a) a protein consisting of the amino acid sequence of SEQ ID NO: 3 or 4;

(b) a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside; and (c) a protein comprising the amino acid sequence of SEQ ID NO: 3 or 4.

2. The method according to claim 1, wherein the steviol glycoside having at least one monoglucoside bond and/or monoglucosyl ester bond is selected from rebaudioside A, stevioside, rubusoside, steviolmonoside, and steviol monoglucosyl ester.

3. The method according to claim 2, wherein the steviol glycoside to be prepared is selected from rebaudioside B and steviolbioside.

4. The method according to claim 1, further comprising culturing a non-human transformant obtained by introducing a polynucleotide selected from the group consisting of polynucleotides (a) to (e) shown below into a host producing a steviol glycoside having at least one monoglucoside bond and/or monoglucosyl ester bond:
   (a) a polynucleotide consisting of the nucleotide sequence of SEQ ID NO: 1;
   (b) a polynucleotide encoding a protein consisting of the amino acid sequence of SEQ ID NO: 3 or 4;
   (c) a polynucleotide encoding a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside;
   (d) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to cleave a monoglucoside bond and/or monoglucosyl ester bond of a steviol glycoside, wherein highly stringent conditions include (i) 5×SSC, 5×Denhardt's solution, 0.5% SDS, 50% formamide, 50° C., (ii) 0.2×SSC, 0.1% SDS, 60° C.; 0.2×SSC, 0.1% SDS, 62° C., or (iii) 0.2×SSC, 0.1% SDS, 65° C.; and
   (e) a polynucleotide encoding a protein comprising the amino acid sequence of SEQ ID NO: 3 or 4.

5. The method according to claim 4, wherein the polynucleotide is inserted into an expression vector.

6. The method according to claim 4, wherein the transformant is transformed koji mold, transformed yeast, or a transformed plant.

7. The method according to claim 1, wherein the protein is derived from a non-human transformed cell obtained by introducing, into a host cell, a polynucleotide selected from the group consisting of polynucleotides (a) to (e) shown below, with a steviol glycoside having at least one monoglucoside bond and/or monoglucosyl ester bond, thereby cleaving said monoglucoside bond and/or monoglucosyl ester bond:
   (a) a polynucleotide consisting of the nucleotide sequence of SEQ ID NO: 1;
   (b) a polynucleotide encoding a protein consisting of the amino acid sequence of SEQ ID NO: 3 or 4;
   (c) a polynucleotide encoding a protein having an amino acid sequence having 90% or more sequence identity to the amino acid sequence of SEQ ID NO: 3 or 4, and having an activity to cleave a monoglucoside bond and/or monoglucosyl ester bond of a steviol glycoside;
   (d) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to cleave a monoglucoside bond and/or monoglucosyl ester bond of a steviol glycoside, wherein highly stringent conditions include (i) 5×SSC, 5×Denhardt's solution, 0.5% SDS, 50% formamide, 50° C., (ii) 0.2×SSC, 0.1% SDS, 60° C.; 0.2×SSC, 0.1% SDS, 62° C., or (iii) 0.2×SSC, 0.1% SDS, 65° C.; and
   (e) a polynucleotide encoding a protein comprising the amino acid sequence of SEQ ID NO: 3 or 4.

8. The method according to claim 7, wherein the polynucleotide is inserted into an expression vector.

9. The method according to claim 7, wherein the transformed cell is transformed koji mold, a transformed bacterium, or transformed yeast.

10. The method according to claim 7, wherein the steviol glycoside having at least one monoglucoside bond and/or monoglucosyl ester bond is selected from rebaudioside A, stevioside, rubusoside, steviolmonoside, and steviol monoglucosyl ester.

11. The method according to claim 10, wherein the steviol glycoside to be prepared is selected from rebaudioside B and steviolbioside.

12. The method according to claim 1, further comprising reacting a protein selected from the group consisting of proteins (d) to (f) shown below, and a steviol glycoside having an unbranched β-1,2-glucoside bond:
   (d) a protein consisting of the amino acid sequence of SEQ ID NO: 7 or 8;
   (e) a protein having an amino acid sequence having 90% or more sequence identity to the amino acid sequence of SEQ ID NO: 7 or 8, and having an activity to cleave an unbranched β-1,2-glucoside bond of a steviol glycoside; and
   (f) a protein comprising the amino acid sequence of SEQ ID NO: 7 or 8.

13. The method according to claim 12, wherein the steviol glycoside having the unbranched β-1,2-glucoside bond comprises one or more steviol glycosides selected from rebaudioside D, rebaudioside E, stevioside, and steviolbioside.

* * * * *